(12) United States Patent
Nesvadba et al.

(10) Patent No.: US 7,619,050 B2
(45) Date of Patent: Nov. 17, 2009

(54) ALKOXYAMINES CONTAINING A RADICALLY POLYMERIZABLE GROUP

(75) Inventors: Peter Nesvadba, Marly (CH); Andreas Kramer, Meyriez (CH); Lucienne Bugnon, Pfeffingen (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 607 days.

(21) Appl. No.: 11/596,436

(22) PCT Filed: May 17, 2005

(86) PCT No.: PCT/EP2005/052260

§ 371 (c)(1),
(2), (4) Date: Nov. 14, 2006

(87) PCT Pub. No.: WO2005/118651

PCT Pub. Date: Dec. 15, 2005

(65) Prior Publication Data

US 2007/0232768 A1 Oct. 4, 2007

(30) Foreign Application Priority Data

May 27, 2004 (EP) .................................. 04102337

(51) Int. Cl.
*C08F 4/00* (2006.01)
(52) U.S. Cl. ................ 526/204; 526/193; 544/86; 544/383; 546/188; 546/247; 546/248; 560/169
(58) Field of Classification Search ............ 526/193, 526/204; 544/86, 383; 546/188, 247, 248; 560/169
See application file for complete search history.

(56) References Cited

U.S. PATENT DOCUMENTS

| | | | | |
|---|---|---|---|---|
| 6,573,346 B1 * | 6/2003 | Melchiors et al. | ............ | 526/217 |
| 6,680,362 B1 * | 1/2004 | Fansler et al. | ............... | 526/217 |
| 6,875,831 B1 * | 4/2005 | Kramer et al. | .............. | 526/209 |
| 6,936,670 B2 * | 8/2005 | Kramer et al. | .............. | 526/265 |
| 7,288,613 B2 * | 10/2007 | Nesvadba et al. | ........... | 526/204 |

FOREIGN PATENT DOCUMENTS

WO 01/02345 1/2001

OTHER PUBLICATIONS

Von Werne et al., J. Amer. Chem. Soc. vol. 125, (Mar. 2003) pp. 3831-3838.
Patent abstracts of Japan, vol. 2003, No. 12, Dec. 2003 of JP 2003 268027.
Chemical Abstract Service, AN 2003:750737 of JP 2003 268027.

* cited by examiner

*Primary Examiner*—Helen L. Pezzuto
(74) *Attorney, Agent, or Firm*—Joseph C. Suhadolnik

(57) ABSTRACT

The instant invention relates to novel alkoxyamine initiators/regulators containing an ethylenically unsaturated, radically polymerizable group. The compounds are useful for the preparation of complex polymeric architectures. Further aspects of the invention are a polymerizable composition and a polymerization process comprising the alkoxyamine initiators/regulators, a macroinitiator obtainable by said polymerization process and a process for polymerizing with the macroinitiator.

19 Claims, No Drawings

ALKOXYAMINES CONTAINING A RADICALLY POLYMERIZABLE GROUP

The instant invention relates to novel alkoxyamine initiators/regulators containing an ethylenically unsaturated, radically polymerizable group. The compounds are useful for the preparation of complex polymeric architectures. Further aspects of the invention are a polymerizable composition and a polymerization process comprising the alkoxyamine initiators/regulators, a macroinitiator obtainable by said polymerization process and a process for polymerizing with the macroinitiator.

Nitroxide mediated free radical polymerization (NMP) has been the object of intensive academic and industrial research during the last years. Hawker et al., J. Am. Chem. Soc. 2003, 125, 3831-3838, for example, describe the use of nitroxide mediated free radical polymerization in designing nanoscopic features of graft polymers. JP2003 268027 describes a polymeric alkoxyamine initiator useful for the preparation of block or graft copolymers.

The control in NMP is due to the reversible capping of propagating radicals with nitroxides to form the so-called dormant species. The field has been reviewed recently by Hawker C J, Bosman A W, Harth E, Chem. Rev. 101: 3661 (2001). The originally widely used, readily available, 2,2,6,6-tetramethyl-1-piperidinoxyl (TEMPO) works reasonably well in styrene and its derivatives but is unsatisfactory for the controlled polymerization of other monomers such as acrylates. Superior results were obtained with recently developed cyclic nitroxides or related alkoxyamines derived from sterically highly hindered piperazinones, piperidines or 7-resp. 8-membered diazepanones as described by Marque S, Sobek J, Fischer H, Kramer A, Nesvadba P, Wunderlich W, Macromolecules 36:3440 (2003). Other classes are dioxathiazocanes or azopanones and azocanones. On the other hand, successful NMP of a broad range of monomers such as e.g. styrene, acrylates acryl amide, acrylonitrile, 1,3-dienes or maleic anhydride was achieved with open-chain, β-hydrido nitroxides such as N-t-butyl-1-diethylphosphono-2,2-dimethylpropylnitroxide, N-t-butyl-isopropylphenylmethyl-nitroxide and the related alkoxyamines, and to a lesser extent with di-t-butyl-nitroxide (DTBN).

Besides of preparing simple homopolymers, synthesis of more complex polymeric architectures is of high interest. Numerous examples have been described. For instance WO 01/02345 and WO 03/004471 disclose multifunctional alkoxyamines based on polyalkylpiperidines, polyalkylpiperazinones and polyalkylmorpholinones and their use for the preparation of complex polymeric architectures such as e.g. star polymers.

There is, however, still a need for new, easily available alkoxyamine initiators useful for the preparation of complex polymeric architectures starting from a wide range of monomers, such as for example styrenic, acrylic, methacrylic and diene-type monomers. The instant invention provides alkoxyamines bearing, for example, acrylate or methacrylate groups. The conventional radical polymerization or copolymerization of these groups allows the preparation of macroinitiators which can be used to make complex polymeric architectures, such as for example block(co)polymers, comb(co)polymers, star(co)polymers, dendritic(co)polymers or hyperbranched(co)polymers.

One aspect of the invention is a compound of formula (I), (II) or (III)

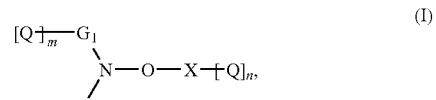

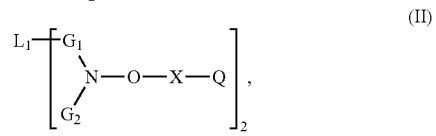

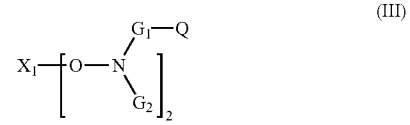

wherein Q is

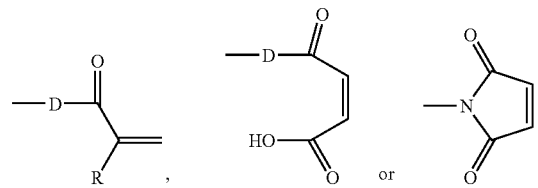

wherein
R is independently H or $C_1$-$C_4$alkyl;
D is O or $NR_3$;
in formula (I) m and n independently are a number 0 or 1 wherein at least one of both is 1;
if in formula (I) m=0 and n=1

X is

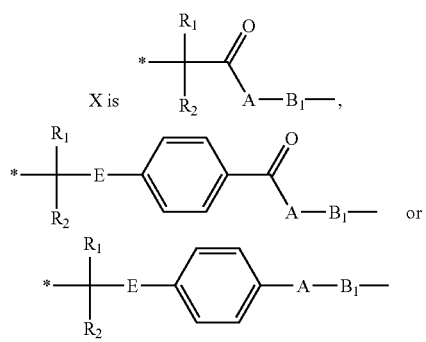

wherein
* denotes where the group is attached to the oxygen atom;
A is O or $NR_3$;
$B_1$ is $C_1$-$C_{25}$alkylene, which may be interrupted by O or $NR_3$ groups, $C_5$-$C_7$cycloalkylene which can contain O and or $NR_3$ groups in the ring, which both are unsubstituted or substituted by $C_1$-$C_8$alkoxy, halogen or a group —COO($C_1$-$C_{18}$alkyl) or phenylene;
additionally —A—$B_1$— can be a direct bond; or
if A is —O— and D is $NR_3$, $B_1$ can be a direct bond; or
if A is $NR_3$ and D is O or $NR_3$, $B_1$ can be a direct bond;
E is a direct bond or a —C(O)— group;

$R_1$, $R_2$ and $R_3$ are independently H, $C_1$-$C_{18}$alkyl, which is unsubstituted or substituted by $C_1$-$C_8$alkoxy, halogen or a group —COO($C_1$-$C_{18}$alkyl), $C_5$-$C_7$cycloalkyl, which is unsubstituted or substituted by $C_1$-$C_8$alkoxy, halogen or a group —COO($C_1$-$C_{18}$alkyl), phenyl, which is unsubstituted or substituted by $C_1$-$C_8$alkoxy, $C_1$-$C_8$alkyl, halogen or a group —COO($C_1$-$C_{18}$alkyl);

the group

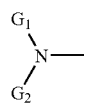

is

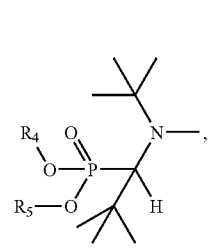 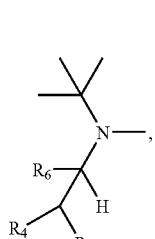 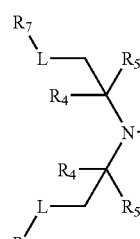

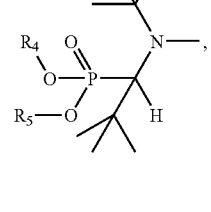 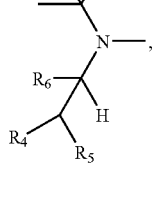 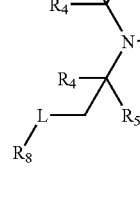

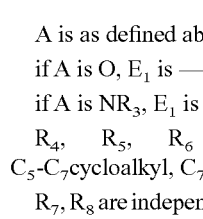 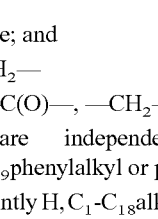 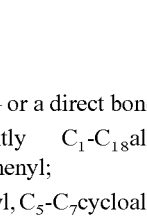

A is as defined above; and
if A is O, $E_1$ is —$CH_2$—
if A is $NR_3$, $E_1$ is —C(O)—, —$CH_2$— or a direct bond;

$R_4$, $R_5$, $R_6$ are independently $C_1$-$C_{18}$alkyl, $C_5$-$C_7$cycloalkyl, $C_7$-$C_9$phenylalkyl or phenyl;

$R_7$, $R_8$ are independently H, $C_1$-$C_{18}$alkyl, $C_5$-$C_7$cycloalkyl, $C_7$-$C_9$phenylalkyl or $C_1$-$C_{18}$acyl;

L is a direct bond, O or $NR_7$;

$R_9$, $R_{10}$ are independently H or $C_1$-$C_{18}$alkoxy, if $R_9$ is H, $R_{10}$ is additionally OH, —O—($C_1$-$C_{18}$)acyl, —$NR_3$—($C_1$-$C_{18}$)acyl or $N(R_3)_2$;

or $R_9$ and $R_{10}$ together with the C-atom to which they are bonded form a cyclic ketale group

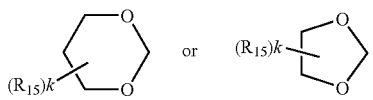

wherein k is 0, 1 or 2 and $R_{15}$ is $C_1$-$C_{18}$alkyl, —$CH_2$—OH or —$CH_2$—O—($C_1$-$C_{18}$)acyl; or $R_9$ and $R_{10}$ together form the group =O, or =N—A—$R_7$;

$R_{11}$, $R_{12}$, $R_{13}$ and $R_{14}$ are independently of each other $C_1$-$C_4$alkyl;

if in formula (I) m=1 and n=1
X is as defined above;
the group

is

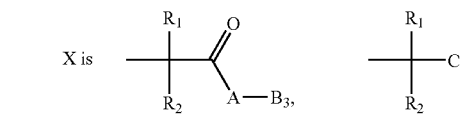

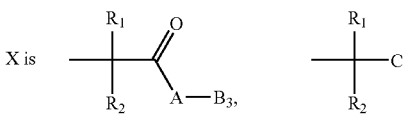

wherein
A and $B_1$ are as defined above;
if in formula (I) m=1 and n=0

X is 

-continued

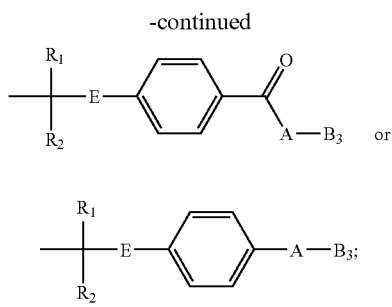

or

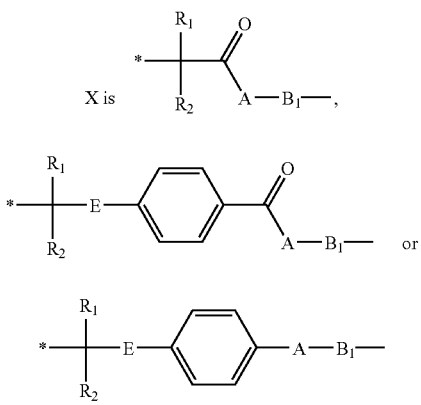

wherein A is O, NR₃ or a direct bond and E, R₁ and R₂ are as defined above;

B₃ is H, C₁-C₂₅alkyl, which may be interrupted by O or NR₃ groups, C₅-C₇cycloalkyl, which can contain O and or NR₃ groups in the ring, which both are unsubstituted or substituted by C₁-C₈alkoxy, halogen or a group —COO(C₁-C₁₈alkyl) or C₁-C₁₈alkoxy or phenyl;

the group

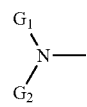

is wherein
A and B₁ are as defined above;
in formula (II)

X is wherein
* denotes where X is attached to the oxygen atom and A, B₁, E, R₁ and R₂ are as defined above;
the group

is

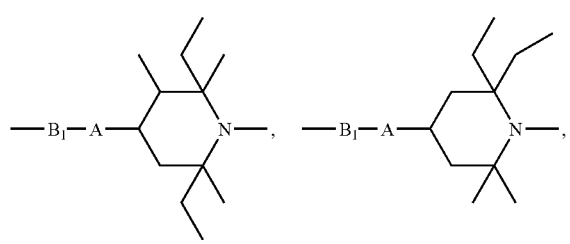

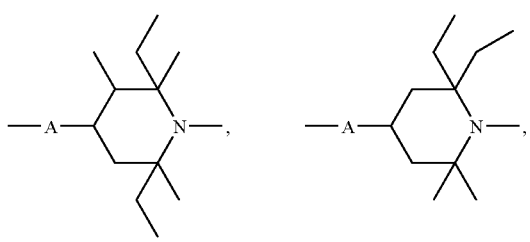

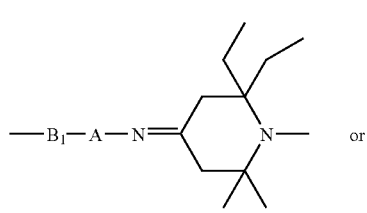

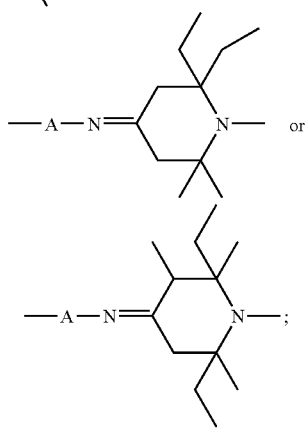

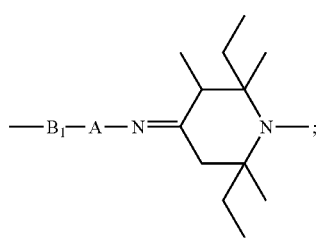

wherein A is as defined above;
L₁ is a divalent group derived from an aliphatic dicarboxylic acid having 2 to 18 carbon atoms from an aromatic dicarboxylic acid or from an aliphatic-aromatic dicarboxylic acid;

in formula (III)

$X_1$ is a group

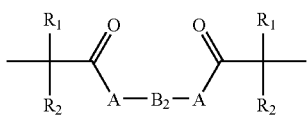

wherein $B_2$ is a direct bond, $C_1$-$C_{25}$alkylene, which may be interrupted by O or $NR_3$ groups, $C_5$-$C_7$cycloalkylene which can contain O and or $NR_3$ groups in the ring, which both are unsubstituted or substituted by $C_1$-$C_8$alkoxy, halogen or a group —COO($C_1$-$C_{18}$alkyl) or phenylene, wherein when $B_2$ is a direct bond one A is O and the other is $NR_3$;

A, $B_1$, $R_1$ and $R_2$ are as defined above and the group

is

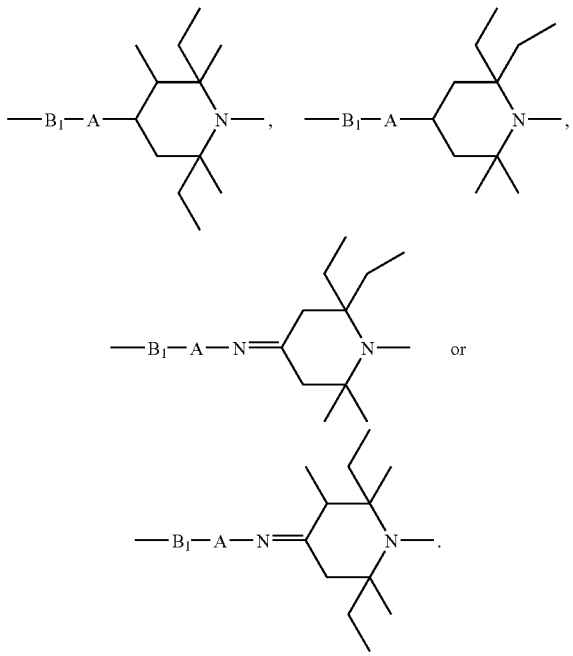

$C_1$-$C_{18}$alkyl is a branched or unbranched radical, such as methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl or octadecyl.

$C_1$-$C_{25}$ alkylene is a branched or unbranched radical, such as methylene, ethylene, propylene, trimethylene, tetramethylene, pentamethylene, hexamethylene, heptamethylene, octamethylene, decamethylene, dodecamethylene, octadecamethylene or eicosamethylene. $C_1$-$C_{12}$alkylene and, in particular, $C_1$-$C_8$alkylene are preferred.

$C_1$-$C_{25}$alkylene, which may be interrupted by O or $NR_3$ groups is, for example, —$CH_2$—O—$CH_2$—, —$CH_2$—NH—$CH_2$—, —$CH_2$—N($CH_3$)—$CH_2$—, —$CH_2$—O—$CH_2CH_2$—O—$CH_2$—, —$CH_2$—(O—$CH_2CH_2$—)$_2$O—$CH_2$—, —$CH_2$—(O—$CH_2CH_2$—)$_3$O—$CH_2$— or —$CH_2$—(O—$CH_2CH_2$—)$_4$O—$CH_2$—.

$C_5$-$C_7$cycloalkylene is a saturated hydrocarbon group having two free valencies and at least one ring unit and is typically cyclopentylene, cyclohexylene or cycloheptylene. Cyclohexylene is preferred.

$C_5$-$C_7$cycloalkylene which can contain O and/or $NR_3$ groups in the ring are for example following groups

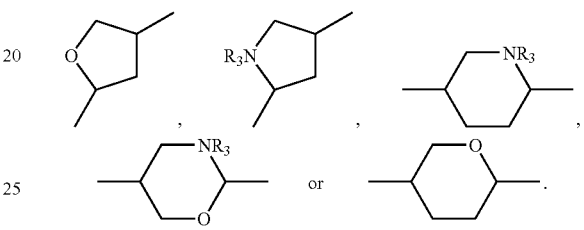

Alkoxy of up to 8 carbon atoms is a branched or unbranched radical, such as methoxy, ethoxy, propoxy, isopropoxy, n-butoxy, isobutoxy, pentoxy, isopentoxy, hexoxy, heptoxy or octoxy.

Halogen is typically chloro, bromo or iodo. Chloro is preferred.

$C_5$-$C_7$cycloalkyl is cyclopentyl, cyclohexyl or cycloheptyl.

$C_7$-$C_9$Phenylalkyl which may be unsubstituted or substituted at the phenyl moiety by 1 to 3 $C_1$-$C_4$-alkyl is typically benzyl, α-methylbenzyl, α,α-dimethylbenzyl, 2-phenylethyl, 2-methylbenzyl, 3-methylbenzyl, 4-methylbenzyl, 2,4-dimethylbenzyl, 2,6-dimethylbenzyl or 4-tert-butylbenzyl. Benzyl is preferred.

$C_1$-$C_{18}$acyl is for example benzoyl or $C_1$-$C_{18}$alkanoyl. Alkanoyl of up to 18 carbon atoms is a branched or unbranched radical, typically formyl, acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl or octadecanoyl. Alkanoyl of 2 to 12, e.g. of 2 to 6, carbon atoms is preferred. Acetyl is particularly preferred.

A divalent group derived from an aliphatic dicarboxylic acid having 2 to 18 carbon atoms is for example derived from oxalic acid, malonic acid, dimethylmalonic acid, succinic acid, pimelic acid, adipic acid, trimethyladipic acid, sebacic acid, azelaic acid and dimeric acids (dimerisation products of unsaturated aliphatic carboxylic acids such as oleic acid), alkylated malonic and succinic acids such as octadecylsuccinic acid.

A divalent group derived from an aliphatic dicarboxylic acid having 2 to 18 carbon atoms is for example derived from terephthalic acid, isophthalic acid, o-phthalic acid, and 1,3-, 1,4-, 2,6- or 2,7-naphthalenedicarboxylic acid, 4,4'-diphenyldicarboxylic acid, 4,4'-diphenylsulfonedicarboxylic acid, 4,4'-benzophenonedicarboxylic acid, 1,1,3-trimethyl-5-carboxyl-3-(p-carboxylphenyl)indane, 4,4'-diphenyl ether dicarboxylic acid, bis-p-(carboxylphenyl)methane or bis-p-(carboxylphenyl)ethane.

For example in the compound of formula (I), (II) or (III)
Q is

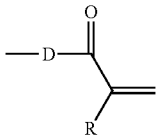

wherein
R is independently H or $C_1$-$C_4$alkyl;
D is O or $NR_3$.

In a specific embodiment the compound is of formula (I), (II) or (III)

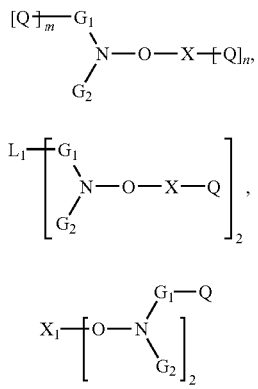

wherein Q is

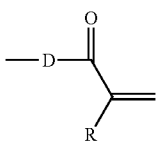

wherein
R is independently H or $C_1$-$C_4$alkyl;
D is O or $NR_3$;
in formula (I) m and n independently are a number 0 or 1 wherein at least one of both is 1;
if in formula (I) m=0 and n=1

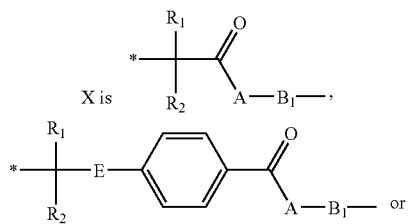

-continued

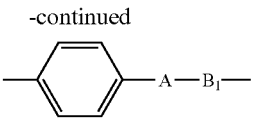

wherein
* denotes where the group is attached to the oxygen atom;
A is O or $NR_3$;
$B_1$ is $C_1$-$C_{25}$alkylene, which may be interrupted by O or $NR_3$ groups, $C_5$-$C_7$cycloalkylene which can contain O and or $NR_3$ groups in the ring, which both are unsubstituted or substituted by $C_1$-$C_8$alkoxy, halogen or a group —COO($C_1$-$C_{18}$alkyl) or phenylene;
additionally —A—$B_1$— can be a direct bond; or
if A is —O— and D is $NR_3$, $B_1$ can be a direct bond; or
if A is $NR_3$ and D is O or $NR_3$, $B_1$ can be a direct bond;
E is a direct bond or a —C(O)— group;
$R_1$, $R_2$ and $R_3$ are independently H, $C_1$-$C_{18}$alkyl, which is unsubstituted or substituted by $C_1$-$C_8$alkoxy, halogen or a group —COO($C_1$-$C_{18}$alkyl), $C_5$-$C_7$cycloalkyl, which is unsubstituted or substituted by $C_1$-$C_8$alkoxy, halogen or a group —COO($C_1$-$C_{18}$alkyl), phenyl, which is unsubstituted or substituted by $C_1$-$C_8$alkoxy, $C_1$-$C_8$alkyl, halogen or a group —COO($C_1$-$C_{18}$alkyl);
the group

is wherein
A is as defined above; and
if A is O, $E_1$ is —$CH_2$—
if A is $NR_3$, $E_1$ is —C(O)—, —$CH_2$— or a direct bond;
$R_7$ is H, $C_1$-$C_{18}$alkyl, $C_5$-$C_7$cycloalkyl, $C_7$-$C_9$phenylalkyl or $C_1$-$C_{18}$acyl;
$R_9$, $R_{10}$ are independently H or $C_1$-$C_{18}$alkoxy,
if $R_9$ is H, $R_{10}$ is additionally OH, —O—($C_1$-$C_{18}$)acyl, —$NR_3$—($C_1$-$C_{18}$)acyl or $N(R_3)_2$;

or $R_9$ and $R_{10}$ together with the C-atom to which they are bonded form a cyclic ketale group

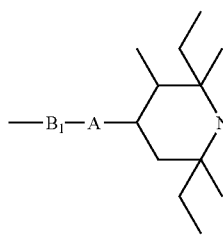

wherein k is 0, 1 or 2 and $R_{15}$ is $C_1$-$C_{18}$alkyl, —$CH_2$—OH or —$CH_2$—O—($C_1$-$C_{18}$)acyl; or $R_9$ and $R_{10}$ together form the group =O, or =N—A—$R_7$;

$R_{11}$, $R_{12}$, $R_{13}$ and $R_{14}$ are independently of each other $C_1$-$C_4$alkyl;

if in formula (I) m=1 and n=1

X is as defined above;

the group

is

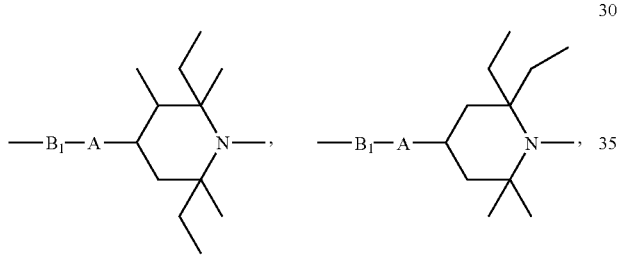

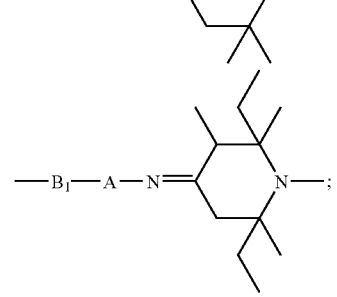

wherein

A and $B_1$ are as defined above;

if in formula (I) m=1 and n=0

X is 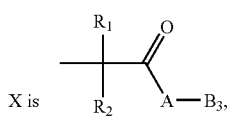 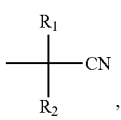

-continued

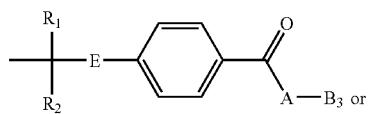

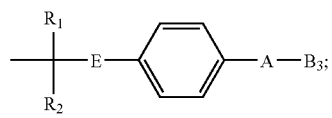

wherein A is O, $NR_3$ or a direct bond and E, $R_1$ and $R_2$ are as defined above;

$B_3$ is H, $C_1$-$C_{25}$alkyl, which may be interrupted by O or $NR_3$ groups, $C_5$-$C_7$cycloalkyl, which can contain O and or $NR_3$ groups in the ring, which both are unsubstituted or substituted by $C_1$-$C_8$alkoxy, halogen or a group —COO($C_1$-$C_{18}$alkyl) or $C_1$-$C_{18}$alkoxy or phenyl;

the group

is

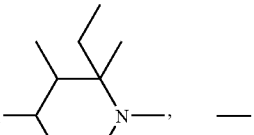
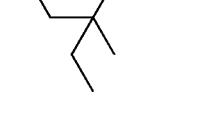
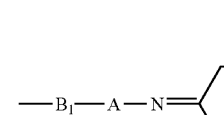
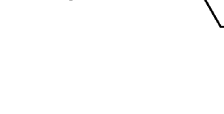
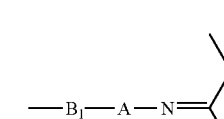
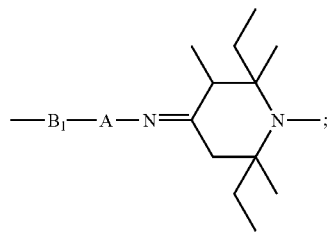

wherein
A and $B_1$ are as defined above;
in formula (II)

X is 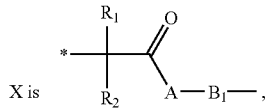,

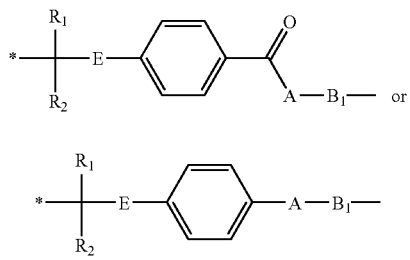 or wherein
* denotes where X is attached to the oxygen atom and A, $B_1$, E, $R_1$ and $R_2$ are as defined above;
the group

is

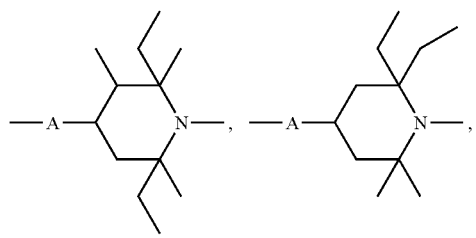

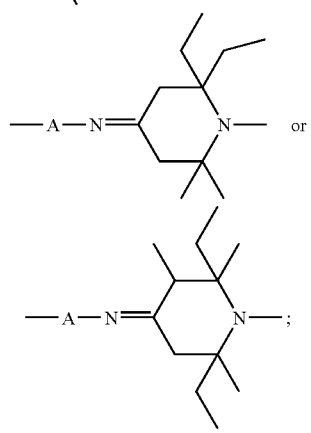

wherein A is as defined above;
$L_1$ is a divalent group derived from an aliphatic dicarboxylic acid having 2 to 18 carbon atoms from an aromatic dicarboxylic acid or from an aliphatic-aromatic dicarboxylic acid;

in formula (III)
$X_1$ is a group

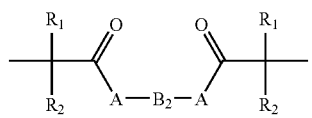

wherein $B_2$ is a direct bond, $C_1$-$C_{25}$alkylene, which may be interrupted by O or $NR_3$ groups, $C_5$-$C_7$cycloalkylene which can contain O and or $NR_3$ groups in the ring, which both are unsubstituted or substituted by $C_1$-$C_8$alkoxy, halogen or a group —COO($C_1$-$C_{18}$alkyl) or phenylene, wherein when $B_2$ is a direct bond one A is O and the other is $NR_3$;
A, $B_1$, $R_1$ and $R_2$ are as defined above and
the group

is

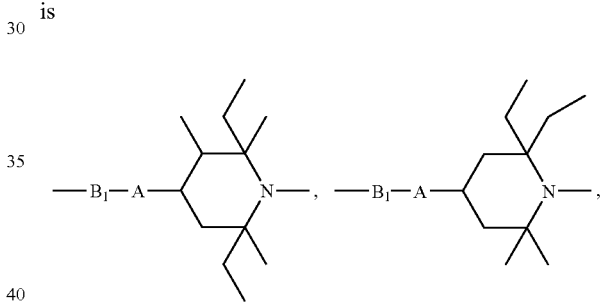

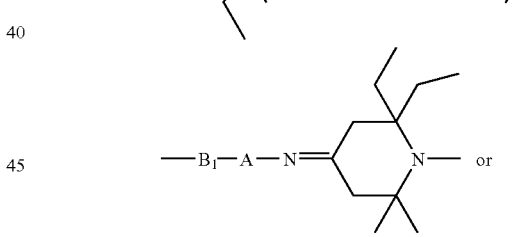

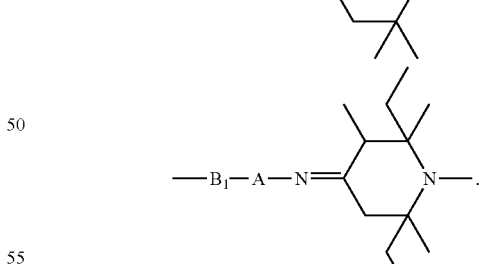

Preference is given to compounds of formula (Ia)

(Ia)

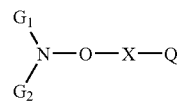

wherein

Q is

[structures: —O—C(=O)—C(R)=CH₂ ; —NR—C(=O)—C(R)=CH₂]

wherein R is independently H or $C_1$-$C_4$alkyl;

X is

[structure: *—C(R₁)(R₂)—C(=O)—A—B₁—]

[structure: *—C(R₁)(R₂)—E—C₆H₄—C(=O)—A—B₁— or]

[structure: *—C(R₁)(R₂)—E—C₆H₄—A—B₁—]

wherein

* denotes where X is attached to the oxygen atom;

A is O or $NR_3$;

$B_1$ is $C_1$-$C_{25}$alkylene, which may be interrupted by O or $NR_3$ groups, $C_5$-$C_7$cycloalkylene which can contain O and or $NR_3$ groups in the ring, which both are unsubstituted or substituted by $C_1$-$C_8$alkoxy, halogen or a group —COO($C_1$-$C_{18}$alkyl) or phenylene;

additionally —A—$B_1$— can be a direct bond; or if A is —O— and D is $NR_3$, $B_1$ can be a direct bond; or if A is $NR_3$ and D is O or $NR_3$, $B_1$ can be a direct bond;

E is a direct bond;

$R_1$, $R_2$ are H or $CH_3$;

$R_3$ is H, $C_1$-$C_{18}$alkyl, $C_5$-$C_6$cycloalkyl or phenyl;

the group

[structure: G₁—N(—)—G₂]

is

[structures with R₄, R₅, R₆, etc., phosphonate and amine groups]

-continued

[piperidine and related N-containing ring structures with R₇, R₈, R₉, R₁₀, L, R₄, R₅ substituents]

[additional piperidine structures with R₉, R₁₀]

[structures with R₁₁, R₁₂, R₁₃, R₁₄, E₁, A and diazepanone with R₇]

wherein

A is as defined above; and if A is O, $E_1$ is —$CH_2$— if A is $NR_3$, $E_1$ is —C(O)—, —$CH_2$— or a direct bond;

$R_4$, $R_5$, are methyl;

$R_7$, $R_8$ are independently H, $C_1$-$C_{18}$alkyl, $C_5$-$C_7$cycloalkyl, benzyl or $C_1$-$C_{18}$acyl;

L is a direct bond, O or $NR_7$;

$R_9$, $R_{10}$ are independently H or $C_1$-$C_{18}$alkoxy, if $R_9$ is H, $R_{10}$ is additionally OH, —O—($C_1$-$C_{18}$)acyl, —$NR_3$—($C_1$-$C_{18}$)acyl or $N(R_3)_2$;

or $R_9$ and $R_{10}$ together with the C-atom to which they are bonded form a cyclic ketale group

[structures: dioxane and dioxolane with ($R_{15}$)$_k$]

wherein k is 0, 1 or 2 and $R_{15}$ is $C_1$-$C_{18}$alkyl, —$CH_2$—OH or —$CH_2$—O—($C_1$-$C_{18}$)acyl; or $R_9$ and $R_{10}$ together form the group =O, or =N—A—$R_7$ $R_{11}$, $R_{12}$, $R_{13}$ and $R_{14}$ are independently of each other $C_1$-$C_4$alkyl.

For instance in the compounds of formula (Ia)

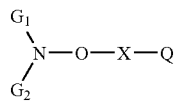
(Ia)

Q is

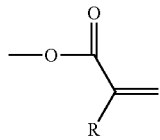

wherein R is H or $C_1$-$C_4$alkyl;

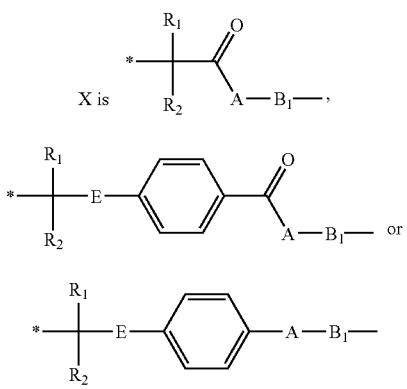

wherein
* denotes where X is attached to the oxygen atom;
A is O or $NR_3$;
$B_1$ is $C_1$-$C_{25}$alkylene, which may be interrupted by O or $NR_3$ groups, $C_5$-$C_7$cycloalkylene which can contain O and or $NR_3$ groups in the ring, which both are unsubstituted or substituted by $C_1$-$C_8$alkoxy, halogen or a group —COO($C_1$-$C_{18}$alkyl) or phenylene;
additionally —A—$B_1$— can be a direct bond; or
if A is —O— and D is $NR_3$, $B_1$ can be a direct bond; or
if A is $NR_3$ and D is O or $NR_3$, $B_1$ can be a direct bond;
E is a direct bond;
$R_1$, $R_2$ are H or $CH_3$;
$R_3$ is H, $C_1$-$C_{18}$alkyl, $C_5$-$C_6$cycloalkyl or phenyl;
the group

is

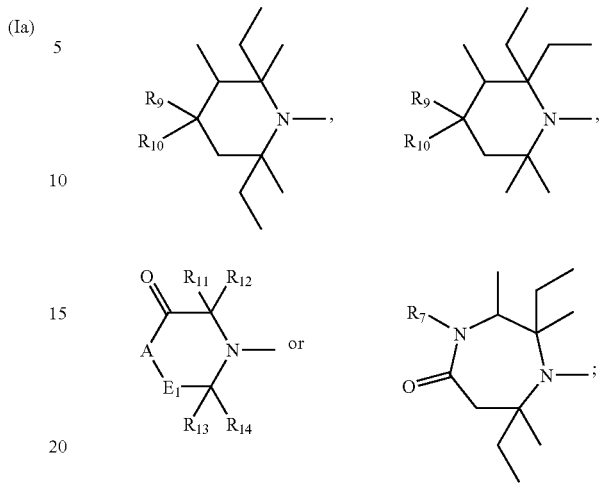

wherein
A is as defined above; and
if A is O, $E_1$ is —$CH_2$—
if A is $NR_3$, $E_1$ is —C(O)—, —$CH_2$— or a direct bond;
$R_7$ is H, $C_1$-$C_{18}$alkyl, $C_5$-$C_7$cycloalkyl, benzyl or $C_1$-$C_{18}$acyl;
$R_9$, $R_{10}$ are independently H or $C_1$-$C_{18}$alkoxy,
if $R_9$ is H, $R_{10}$ is additionally OH, —O—($C_1$-$C_{18}$)acyl, —$NR_3$—($C_1$-$C_{18}$)acyl or $N(R_3)_2$;
or
$R_9$ and $R_{10}$ together with the C-atom to which they are bonded form a cyclic ketale group

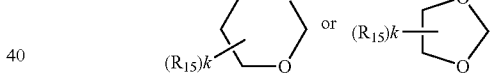

wherein k is 0, 1 or 2 and $R_{15}$ is $C_1$-$C_{18}$alkyl, —$CH_2$—OH or —$CH_2$—O—($C_1$-$C_{18}$)acyl; or
$R_9$ and $R_{10}$ together form the group =O, or =N—O—$R_7$;
$R_{11}$, $R_{12}$, $R_{13}$ and $R_{14}$ are independently of each other $C_1$-$C_4$alkyl.

Special preference is given to compounds of formula (Ia)

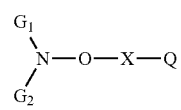
(Ia)

wherein
Q is

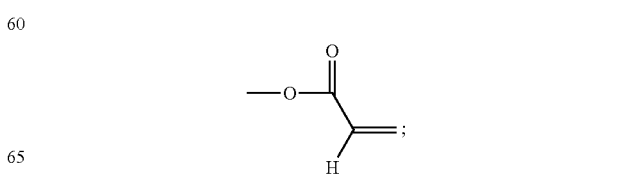

X is

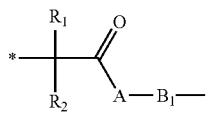

wherein
* denotes where X is attached to the oxygen atom;
A is O or $NR_3$;
$B_1$ is $C_1$-$C_{18}$alkylene, or phenylene;
$R_1$, $R_2$ are H or $CH_3$;
$R_3$ is H, $C_1$-$C_4$alkyl or phenyl;
the group

is

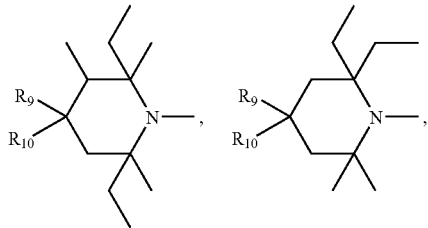

$R_9$, $R_{10}$ are independently H or $C_1$-$C_{18}$alkoxy, or
if $R_9$ is H, $R_{10}$ is additionally OH, —O—($C_1$-$C_{18}$)acyl, —$NR_3$—($C_1$-$C_{18}$)acyl or $N(R_3)_2$;
or
$R_9$ and $R_{10}$ together with the C-atom to which they are bonded form a cyclic ketale group

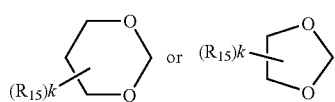

wherein k is 0, 1 or 2 and $R_{15}$ is $C_1$-$C_{18}$alkyl, —$CH_2$—OH or —$CH_2$—O—($C_1$-$C_{18}$)acyl; or
$R_9$ and $R_{10}$ together form the group =O, or =N—O—$R_7$.
Particularly preferred are compounds of formula (Ia)

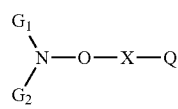
(Ia)

wherein
Q is

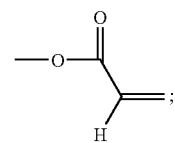

X is

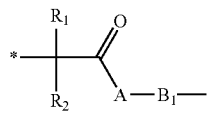

wherein
* denotes where X is attached to the oxygen atom;
A is O or $NR_3$;
$B_1$ is $C_1$-$C_4$alkylene, or phenylene;
$R_1$, $R_2$ are H or $CH_3$;
$R_3$ is H, $C_1$-$C_4$alkyl or phenyl;
the group

is

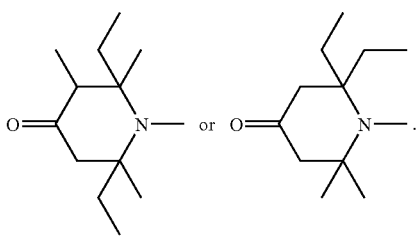

Specific individual compounds are:
a) Acrylic acid 2-[2-(2,6-diethyl-4-hydroxy-2,3,6-trimethyl-piperidin-1-yloxy)-propionyloxy]-ethyl ester
b) Acrylic acid 2-[2-(2,6-diethyl-2,3,6-trimethyl-4-oxo-piperidin-1-yloxy)-propionyloxy]-ethyl ester
c) Acrylic acid 2-[2-(2,6-diethyl-2,3,6-trimethyl-4-oxo-piperidin-1-yloxy)-2-methyl-propionylamino]-ethyl ester
d) Acrylic acid 1-(1-{6-[2-(4-acryloyloxy-2,6-diethyl-2,3,6-trimethyl-piperidin-1-yloxy)-propionylamino]-hexylcarbamoyl}-ethoxy)-2,6-diethyl-2,3,6-trimethyl-piperidin-4-yl ester
e) 2-Methyl-acrylic acid 2-[2-(2,6-diethyl-2,3,6-trimethyl-4-oxo-piperidin-1-yloxy)-propionylamino]-ethyl ester
f) Acrylic acid 2-[2-(4-tert-butyl-2,2-diethyl-6,6-dimethyl-3-oxo-piperazin-1-yloxy)-propionylamino]-ethyl ester
g) Acrylic acid 2-(2-{N-tert-butyl-N-[1-(diethoxy-phosphoryl)-2,2-dimethyl-propyl]-aminooxy}-propionylamino)-ethyl ester
h) Acrylic acid 2-[2-(4-acryloyloxy-2,6-diethyl-2,3,6-trimethyl-piperidin-1-yloxy)-propionylamino]-ethyl ester i) Terephthalic acid bis-{1-[1-(2-acryloyloxy-ethylcarbamoyl)-ethoxy]-2,6-diethyl-2,3,6-trimethyl-piperidin-4-yl}ester j) 2-Methyl-acrylic acid 2-[2-(2,6-diethyl-2,3,6-trimethyl-4-oxo-piperidin-1-yloxy)-propionyloxy]-ethyl ester k) 2-Methyl-acrylic acid 1-[1-(2-acryloyloxy-ethoxycarbonyl)-ethoxy]-2,6-diethyl-2,3,6-trimethyl-piperidin-4-yl ester l) Acrylic acid 2-[2-(4-acryloyloxy-2,6-diethyl-2,3,6-trimethyl-piperidin-1-yloxy)-propionyloxy]-ethyl ester m) Acrylic acid 2-{(2-acryloyloxy-ethyl)-[2-(2,6-diethyl-2,3,6-trimethyl-4-oxo-piperidin-1-yloxy)-propionyl]-amino}-ethyl ester.

The compounds of the present invention have all an ethylenically unsaturated bond and in addition a —O—N< group. They can therefore be used as monomers in a conventional radical polymerization process, preferably together with further ethylenically unsaturated monomers and as initiators/regulators in controlled radical polymerization processes.

Both processes can be carried out independently of each other or in a consecutive manner.

When the compounds of the present invention are used in a controlled polymerization process, the resulting polymer or copolymer has typically a polydispersity index of 1.0 to 2.0, preferably from 1.1 to 1.7 and in particular from 1.1 to 1.5.

A further aspect of the invention is a polymerizable composition comprising a) at least one ethylenically unsaturated monomer;

b) a radical polymerization initiator; and c) a compound of formula (I), (II) or (III) as described above.

The ethylenically unsaturated monomer of component a) can be chosen from a variety of monomers. Such as isoprene, 1,3-butadiene, $\alpha$-$C_5$-$C_{18}$alkene, styrene, $\alpha$-methyl styrene, p-methyl styrene p-tert-butyl-styrene or a compound of formula $CH_2$=$C(R_a)$—(C=Z)—$R_b$, wherein $R_a$ is hydrogen or $C_1$-$C_4$alkyl, $R_b$ is $NH_2$, $O^-(Me^+)$, unsubstituted $C_1$-$C_{18}$alkoxy, $C_2$-$C_{100}$alkoxy interrupted by at least one N and/or O atom, or hydroxy-substituted $C_1$-$C_{18}$alkoxy, unsubstituted $C_1$-$C_{18}$alkylamino, di($C_1$-$C_{18}$alkyl)amino, hydroxy-substituted $C_1$-$C_{18}$alkylamino or hydroxy-substituted di($C_1$-$C_{18}$alkyl)amino, —O—$CH_2$—$CH_2$—$N(CH_3)_2$ or —O—$CH_2$—$CH_2$—$N^+H(CH_3)_2$ $An^-$;

$An^-$ is a anion of a monovalent organic or inorganic acid;

Me is a monovalent metal atom or the ammonium ion.

Z is oxygen or sulfur.

Examples for $R_a$ as $C_2$-$C_{100}$alkoxy interrupted by at least one O atom are of formula

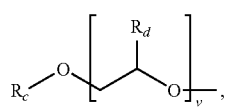

wherein $R_c$ is $C_1$-$C_{25}$alkyl, phenyl or phenyl substituted by $C_1$-$C_{18}$alkyl, $R_d$ is hydrogen or methyl and v is a number from 1 to 50. These monomers are for example derived from non ionic surfactants by acrylation of the corresponding alkoxylated alcohols or phenols. The repeating units may be derived from ethylene oxide, propylene oxide or mixtures of both.

Further examples of suitable acrylate or methacrylate monomers are given below.

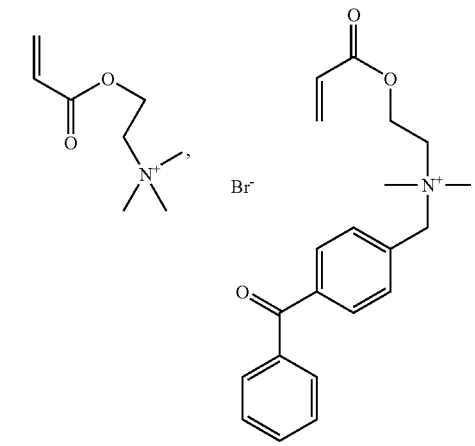

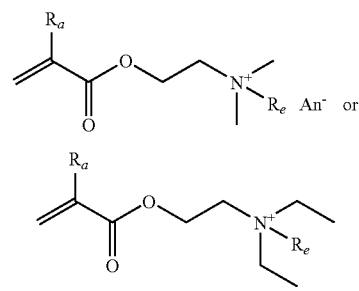

$An^-$, wherein $An^-$ and $R_a$ have the meaning as defined above and $R_e$ is methyl, benzyl or benzoylbenzyl. $An^-$ is preferably $Cl^-$, $Br^-$ or $^-O_3S$—O—$CH_3$.

Further acrylate monomers are

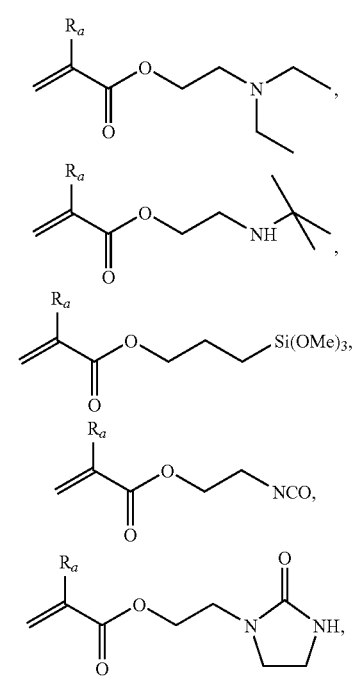

-continued

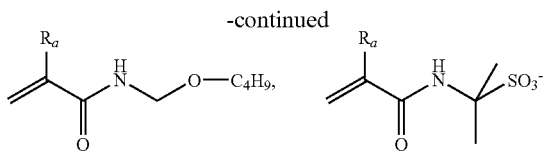

Me⁺, Me⁺ is an alkali metal cation or the ammonium cation.

Examples for suitable monomers other than acrylates are

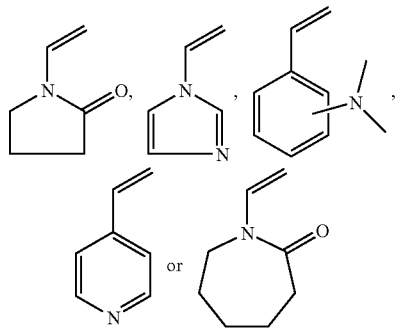

Preferably $R_a$ is hydrogen or methyl, $R_b$ is $NH_2$, gycidyl, unsubstituted or with hydroxy substituted $C_1$-$C_4$alkoxy, unsubstituted $C_1$-$C_4$alkylamino, di($C_1$-$C_4$alkyl)amino, hydroxy-substituted $C_1$-$C_4$alkylamino or hydroxy-substituted di($C_1$-$C_4$alkyl)amino; and Z is oxygen.

For example the ethylenically unsaturated monomer is selected from the group consisting of ethylene, propylene, n-butylene, i-butylene, styrene, substituted styrene, conjugated dienes, acrolein, vinyl acetate, vinylpyrrolidone, vinylimidazole, maleic anhydride, (alkyl)acrylic acidanhydrides, (alkyl)acrylic acid salts, (alkyl)acrylic esters, (alkyl) acrylonitriles, (alkyl)acrylamides, vinyl halides or vinylidene halides.

For instance the ethylenically unsaturated monomer is styrene, substituted styrene, methylacrylate, ethylacrylate, butylacrylate, isobutylacrylate, tert. butylacrylate, hydroxyethylacrylate, hydroxypropylacrylate, dimethylaminoethylacrylate, methyl(meth)acrylate, ethyl (meth)acrylate, butyl(meth)acrylate, hydroxyethyl(meth) acrylate, hydroxypropyl(meth)acrylate, dimethylaminoethyl (meth)acrylate, acrylonitrile, methacrylonitrile, acrylamide, methacrylamide or dimethylaminopropyl-methacrylamide.

Very suitable monomers are for example styrene, $C_1$-$C_8$alkylesters of acrylic or methacrylic acid, such as n-butylacrylate or methacrylate, acrylonitrile or methacrylonitrile, in particular styrene, acrylonitrile and n-butylacrylate.

It is also possible to use mixtures of the afore mentioned monomers, in particular styrene/acrylonitrile, styrene/butylacrylate, styrene/methylmethacrylate and styrene/butylmethacrylate.

Preference is given to a polymerizable composition wherein the ethylenically unsaturated monomer is a compound of formula $CH_2=C(R_a)-(C=Z)-R_b$, wherein Z is O or S;

$R_a$ is hydrogen or $C_1$-$C_4$alkyl;

$R_b$ is $NH_2$, $O^-(Me^+)$, glycidyl, unsubstituted $C_1$-$C_{18}$alkoxy, $C_2$-$C_{100}$alkoxy interrupted by at least one N and/or O atom, or hydroxy-substituted $C_1$-$C_{18}$alkoxy, unsubstituted $C_1$-$C_{18}$alkylamino, di($C_1$-$C_{18}$alkyl)amino, hydroxy-substituted $C_1$-$C_{18}$alkylamino or hydroxy-substituted di($C_1$-$C_{18}$alkyl)amino, $-O-CH_2-CH_2-N(CH_3)_2$ or $-O-CH_2-CH_2-N^+H(CH_3)_2 An^-$;

$An^-$ is a anion of a monovalent organic or inorganic acid;

Me is a monovalent metal atom or the ammonium ion.

For example the radical polymerization initiator, component b) is a azo compound, a peroxide, a perester or a hydroperoxide.

Specific preferred radical initiators are 2,2'-azobisisobutyronitrile, 2,2'-azobis(2-methylbutyronitrile), 2,2'-azobis(2,4-dimethylvaleronitrile), 2,2'-azobis(4-methoxy-2,4-dimethylvaleronitrile), 1,1'-azobis(1-cyclohexanecarbonitrile), 2,2'-azobis(isobutyramide) dihydrate, 2-phenylazo-2,4-dimethyl-4-methoxyvaleronitrile, dimethyl-2,2'-azobisisobutyrate, 2-(carbamoylazo)isobutyronitrile, 2,2'-azobis(2,4,4-trimethylpentane), 2,2'-azobis(2-methylpropane), 2,2'-azobis(N,N'-dimethyleneisobutyramidine), free base or hydrochloride, 2,2'-azobis(2-amidinopropane), free base or hydrochloride, 2,2'-azobis{2-methyl-N-[1,1-bis(hydroxymethyl)ethyl]propionamide} or 2,2'-azobis{2-methyl-N-[1,1-bis(hydroxymethyl)-2-hydroxyethyl]propionamide; acetyl cyclohexane sulphonyl peroxide, diisopropyl peroxy dicarbonate, t-amyl perneodecanoate, t-butyl perneodecanoate, t-butyl perpivalate, t-amylperpivalate, bis(2,4-dichlorobenzoyl)peroxide, diisononanoyl peroxide, didecanoyl peroxide, dioctanoyl peroxide, dilauroyl peroxide, bis(2-methylbenzoyl) peroxide, disuccinic acid peroxide, diacetyl peroxide, dibenzoyl peroxide, t-butyl per 2-ethylhexanoate, bis-(4-chlorobenzoyl)-peroxide, t-butyl perisobutyrate, t-butyl permaleinate, 1,1-bis(t-butylperoxy)3,5,5-trimethylcyclohexane, 1,1-bis(t-butylperoxy)cyclohexane, t-butyl peroxy isopropyl carbonate, t-butyl perisononaoate, 2,5-dimethylhexane 2,5-dibenzoate, t-butyl peracetate, t-amyl perbenzoate, t-butyl perbenzoate, 2,2-bis(t-butylperoxy) butane, 2,2 bis(t-butylperoxy) propane, dicumyl peroxide, 2,5-dimethylhexane-2,5-di-t-butylperoxide, 3-t-butylperoxy 3-phenylphthalide, di-t-amyl peroxide, α,α'-bis(t-butylperoxy isopropyl) benzene, 3,5-bis(t-butylperoxy)3,5-dimethyl 1,2-dioxolane, di-t-butyl peroxide, 2,5-dimethylhexyne-2,5-di-t-butylperoxide, 3,3,6,6,9,9-hexamethyl 1,2,4,5-tetraoxa cyclononane, p-menthane hydroperoxide, pinane hydroperoxide, diisopropylbenzene mono-α-hydroperoxide, cumene hydroperoxide or t-butyl hydroperoxide.

A further aspect of the invention is a process for preparing an oligomer, a cooligomer, a polymer or a copolymer (block, random or graft) by free radical polymerization of at least one ethylenically unsaturated monomer or oligomer, which comprises (co)polymerizing the monomer or monomers/oligomers in the presence of a) a free radical initiator; and
b) a compound of formula (I), (II) or (III) as described above.

The polymerization is carried out by applying heat or electromagnetic radiation from microwaves to γ-radiation.

The polymerization is usually carried out under atmospheric pressure for example for 10 minutes to 16 hours, preferably from 1 hour to 8 hours.

Typically the polymerization is carried out by heating and takes place at a temperature between 0° C. and 160° C., for example between 20° C. and 160° C., for instance between 50° C. and 140° C.

The amount of component b) may vary in a wide range, for example from 1% to 100% by weight, based on the weight of the sum of all ethylenically unsaturated compounds. In many cases 10% to 70% are desirable.

The radical polymerization process as such is known and may be carried out in bulk, in the presence of an organic solvent or in the presence of water or in mixtures of organic solvents and water. Additional cosolvents or surfactants, such as glycols or ammonium salts of fatty acids, may be present. Other suitable cosolvents are described hereinafter.

If organic solvents are used, suitable solvents or mixtures of solvents are typically pure alkanes (hexane, heptane, octane, isooctane), aromatic hydrocarbons (benzene, toluene, xylene), halogenated hydrocarbons (chlorobenzene), alkanols (methanol, ethanol, ethylene glycol, ethylene glycol monomethyl ether), esters (ethyl acetate, propyl, butyl or hexyl acetate) and ethers (diethyl ether, dibutyl ether, ethylene glycol dimethyl ether), anisol, tert-butyl-benzene or mixtures thereof.

When the above described polymerization has been carried out, a polymer or oligomer is obtained, which has attached several —O—N< groups at the polymer backbone. These groups can be used to carry out a controlled radical polymerization starting from the various initiating radicals at the polymer backbone and complex polymer architectures ca be obtained.

Consequently a further aspect of the invention is a polymeric or oligomeric macroinitiator obtainable by a process as described above.

Also an aspect of the invention is a process for preparing a comb, star, tapered or branched polymer or copolymer by controlled free radical polymerization (CFRP), which comprises polymerizing at least one ethylenically unsaturated monomer in the presence of the polymeric macroinitiator obtainable in a process as described above.

Typically the polymerization process is carried out by heating and takes place at a temperature between 80° C. and 160° C.

A further aspect is the use of a polymeric macroinitiator obtainable in a process as described above as radical initiator for the polymerization of ethylenically unsaturated monomers.

The definitions and preferences given for the compounds of formula (I), (II) and (III) apply also for the other aspects of the invention.

The polymers prepared by the present invention are useful for following applications:

adhesives, detergents, dispersants, emulsifiers, surfactants, defoamers, adhesion promoters, corrosion inhibitors, viscosity improvers, lubricants, rheology modifiers, thickeners, crosslinkers, paper treatment, water treatment, electronic materials, paints, coatings, photography, ink materials, imaging materials, superabsorbants, cosmetics, hair products, preservatives, biocide materials or modifiers for asphalt, leather, textiles, ceramics and wood.

Because the present polymerization is a "living" polymerization, it can be started and stopped practically at will. Furthermore, the polymer product retains the functional alkoxyamine group allowing a continuation of the polymerization in a living matter. Thus, in one embodiment of this invention, once the first monomer is consumed in the initial polymerizing step a second monomer can then be added to form a second block on the growing polymer chain in a second polymerization step. Therefore it is possible to carry out additional polymerizations with the same or different monomer(s) to prepare multi-block copolymers.

The following examples illustrate the invention

PREPARATION EXAMPLES A1-A13

Example A1

Acrylic acid 2-[2-(2,6-diethyl-4-hydroxy-2,3,6-trimethyl-piperidin-1-yloxy)-propionyloxy]-ethyl ester (Compound 1, Tab. 1)

A) Acrylic acid 2-(2-bromo-propionyloxy)-ethyl ester

The synthesis of acrylic acid 2-(2-bromo-propionyloxy)-ethyl ester is conducted as reported in Macromolecules, 1197, 30, 5192-94.

B) Compound 1, Tab. 1

To a stirred solution of 99.6 g (0.46 mol) of 2,6-diethyl-1-hydroxy-2,3,6-trimethyl-piperidin-4-one (prepared as described in U.S. Pat. No. 6,353,107 B1, example 2), 66.3 g (0.46 mol) of CuBr and 29.4 g (0.46 mol) Cupper in 1000 ml toluene 160 g (0.92 mol) of N,N,N',N'',N''-pentamethyldiethylenetriamine (PMDTA) are added. The brown suspension is then cooled to 10° C. and 116 g (0.46 mol) of acrylic acid 2-(2-bromo-propionyloxy)-ethyl ester dissolved in 250 ml toluene are added dropwise while keeping the temperature below 15° C. The reaction mixture is stirred for another 12 h at room temperature and then filtered. The filtrate is washed with water (3×500 ml), then with a 10% solution of EDTA (3×500 ml), dried over $NaSO_4$ and evaporated. The residue is chromatographed over Silica gel with hexane-ether (7:3) to afford 165 g of the title compound as slightly yellow oil.

Elemental analysis calculated for $C_{20}H_{35}NO_6$: C, 62.31%; H, 9.15%; N, 3.63%. Found: C, 62.31%; H, 9.28%; N, 3.58%.

Example A2

Acrylic acid 2-[2-(2,6-diethyl-2,3,6-trimethyl-4-oxo-piperidin-1-yloxy)-propionyloxy]-ethyl ester (Compound 2, Tab. 1)

In analogy to Example 1B) are reacted: 42.46 g (0.20 mol) 2,6-diethyl-1-oxy-2,3,6-trimethyl-piperidin-4-one, 50.22 g (0.20 mol) acrylic acid 2-(2-bromo-propionyloxy)-ethyl ester, 28.7 g (0.20 mol) CuBr, 12.7 g (0.20) Cupper and 69.3 g (0.40 mol) PMDTA to afford 54.8 g of the title compound as a colorless oil.

Elemental analysis calculated for $C_{20}H_{33}NO_6$: C, 62.64%; H, 8.67%; N, 3.65%. Found: C, 62.32%; H, 8.79%; N, 3.66%.

Example A3

Acrylic acid 2-[2-(2,6-diethyl-2,3,6-trimethyl-4-oxo-piperidin-1-yloxy)-2-methyl-propionylamino]-ethyl ester (Compound 3, Tab. 1)

B) 2-Bromo-N-(2-hydroxy-ethyl)-2-methyl-propionamide

To a stirred solution of 12.2 g (0.2 mol) of ethanolamine in 50 ml tetrahydrofurane (THF) are at 0° C. added 23.0 g (0.1 mol) of α-isobutyrylbromide. The mixture is then stirred 12 h at room temperature and the THF is then evaporated. To the residue are added 20 ml of water and 7 g of NaCl. The mixture is extracted with 25 ml of each t-butyl-methyl ether and ethylacetate, the extracts are washed with brine, dried over MgSO$_4$ and evaporated to afford 19.9 g of the title compound as a colorless oil.

$^1$H-NMR (300 MHz, CDCl$_3$, δ ppm): 7.17 (bs, 1H), 3.76 (t, 2H), 3.46 (m, 2H), 2.79 (bs, 1H), 1.96 (s, 6H).

C) 2-(2,6-Diethyl-2,3,6-trimethyl-4-oxo-piperidin-1-yloxy)-N-(2-hydroxy-ethyl)-2-methyl-propionamide To a stirred solution of 13.85 g (0.066 mol) of 2-bromo-N-(2-hydroxy-ethyl)-2-methyl-propionamide and 12.74 g (0.06 mol) of 2,6-diethyl-1-oxy-2,3,6-trimethyl-piperidin-4-one (prepared as described in U.S. Pat. No. 6,353,107 B1, example 3) in ethylacetate (50 ml) are under argon added 11.8 g (0.12 mol) CuCl. To the stirred suspension are added dropwise 20.8 g (0.12 mol) of N,N,N',N'',N''-pentamethyidiethylenetriamine (PMDTA) while keeping the temperature below 35° C. The mixture is stirred for another 4 h at room temperature and then filtered. The filtrate is washed with water (3×50 ml), then with 1% solution of EDTA, dried over MgSO$_4$ and evaporated. The residue is chromatographed over Silica gel with hexane-ethylacetate (1:1 to 1:3) to afford 17.5 g of the title compound as a colorless oil.

$^1$H-NMR (300 MHz, CDCl$_3$, δ ppm): 6.87-6.86 (bs, 1H), 3.73 (m, 2H), 3.47-3.41 (m, 2H), 2.85-0.80 (m, 29H).

D) Compound 3, Tab. 1

Acryloylchloride (1.67 g, 0.0185 mol) is added dropwise and below 40° C. to a solution of 6.22 g (0.018 mol) of the intermediate prepared under B) and 2.6 ml (0.01852 mol) triethylamine in 30 ml of toluene. Additional 1.2 ml of triethylamine and 0.6 ml of acryloylchloride are added after 2.5 h. The mixture is stirred for 1 h, then washed with 4×10 ml water, dried over MgSO$_4$ and evaporated. Chromatography of the residue over silica gel with hexane-ethyl acetate (2:1) afford 6.45 g of the title compound as a viscous colorless oil.

MS (APCI): calculated C$_{21}$H$_{36}$N$_2$O$_5$ (396.53). found M$^+$=396.

Example A4

Acrylic acid 1-(1-{6-[2-(4-acryloyloxy-2,6-diethyl-2,3,6-trimethyl-piperidin-1-yloxy)-propionylamino]-hexylcarbamoyl}-ethoxy)-2,6-diethyl-2,3,6-trimethyl-piperidin-4-yl ester (Compound 4, Tab. 1)

Acryloylchloride (0.27 g, 3.0 mmol) is added dropwise and below 20° C. to a solution of 0.98 g (1.5 mmol) of 2-(2,6-Diethyl-4-hydroxy-2,3,6-trimethyl-piperidin-1-yloxy)-N-{6-[2-(2,6-diethyl-4-hydroxy-2,3,6-trimethyl-piperidin-1-yloxy)-propionylamino]-hexyl}-propionamide (prepared as described in WO 03/004471 A1, example A3) and 0.3 g (3.0 mmol) triethylamine in 30 ml ethyl acetate. The mixture is stirred for 12 h at room temperature, then washed with 3×10 ml water, dried over Na$_2$SO$_4$ and evaporated. Chromatography of the residue over silica gel with hexane-ethyl acetate (3:2) afford 0.33 g of the title compound as a viscous slightly yellow oil.

MS (APCI): calculated C$_{42}$H$_{74}$N$_4$O$_8$ (763.08). found M$^+$=762.55.

Example 5

2-Methyl-acrylic acid 2-[2-(2,6-diethyl-2,3,6-trimethyl-4-oxo-piperidin-1-yloxy)-propionylamino]-ethyl ester (Compound 5, Tab. 1)

A) 2-Chloro-N-(2-hydroxy-ethyl)-propionamide

Ethanolamine (13.45 g, 0.22 mol) is added to 21.5 ml (0.2 mol) of 2-chloropropionic acid methylester. The mixture solidifies after standing at room temperature for 60 h. The solid is triturated with ethylacetate, the crystals are filtered off and dried to afford 27.75 g of the title compound as white crystals, mp. 64° C.

$^1$H-NMR (300 MHz, CDCl$_3$, δ ppm): 7.09 (bs, 1H), 4.44 (q, 1H), 3.76 (t, 2H), 3.48 (m, 2H), 2.79 (bs, 1H), 1.75 (d. 3H).

B) 2-(2,6-Diethyl-2,3,6-trimethyl-4-oxo-piperidin-1-yloxy)-N-(2-hydroxy-ethyl)-propionamide In analogy to Example 3B) were reacted: 30.35 g (0.143 mol) 2,6-diethyl-1-oxy-2,3,6-trimethyl-piperidin-4-one, 24.35 g (0.157 mol) 2-chloro-N-(2-hydroxy-ethyl)-propionamide, 28.3 g (0.286 mol) CuCl and 49.55 g (0.286 mol) PMDTA to afford 44.8 g of the title compound as a colorless resin.

$^1$H-NMR (300 MHz, CDCl$_3$, δ ppm): 6.80 (bs, 1H), 4.40 (m, 1H), 3.76-0.90 (m, 30H).

C) Compound 5, Tab. 1

In analogy to Example 3C) are reacted: 15.76 g (0.024 mol) 2-(2,6-diethyl-2,3,6-trimethyl-4-oxo-piperidin-1-yloxy)-N-(2-hydroxy-ethyl)-propionamide, 3.0 g (0.028 mol) methacryloyl-chloride and 4.2 ml triethylamine to afford 6.08 g of the title compound as a colorless resin.

MS (APCI): calculated C$_{21}$H$_{36}$N$_2$O$_5$ (396.53). found M$^+$=396.

Example 6

Acrylic acid 2-[2-(4-tert-butyl-2,2-diethyl-6,6-dimethyl-3-oxo-piperazin-1-yloxy)-propionylamino]-ethyl ester (Compound 6, Tab. 1)

A) 2-(4-tert-Butyl-2,2-diethyl-6,6-dimethyl-3-oxo-piperazin-1-yloxy)-N-(2-hydroxy-ethyl)-propionamide In analogy to Example 3B) are reacted 5.0 g (0.033 mol) 2-chloro-N-(2-hydroxy-ethyl)-propionamide, 10.4 g (0.033 mol) PMDETA, 5.94 g (0.06 mol) CuCl and 7.66 g (0.03 mol) 1-tert-butyl-3,3-diethyl-4-oxy-5,5-dimethyl-piperazin-2-one (prepared as described in U.S. Pat. No. 6,479,608 B1) to afford 9.18 g of the title compound as a colorless resin.

$^1$H-NMR (300 MHz, CDCl$_3$, δ ppm): 7.28 (bs, 1H), 4.30 (q, 1H), 3.77 (m, 2H), 3.47 (m, 2H), 3.08 (bs, 1H), 2.0-0.93 (m, 30H).

B) Compound 6, Tab. 1

In analogy to Example 3C) are reacted 7.68 g (0.0207 mol), 2-(4-tert-butyl-2,2-diethyl-6,6-dimethyl-3-oxo-piperazin-1-yloxy)-N-(2-hydroxy-ethyl)-propionamide 2.1 g (0.023 mol) acryloylchloride and 3.4 ml (0.023 mol) triethylamine to afford 6.75 g of the title compound as a colorless resin.

MS (APCI): calculated C$_{22}$H$_{39}$N$_3$O$_5$ (425.57). found M$^+$=425.

Example 7

Acrylic acid 2-(2-{N-tert-butyl-N-[1-(diethoxy-phosphoryl)-2,2-dimethyl-propyl]-aminooxy}-propionylamino)-ethyl ester (Compound 7, Tab. 1)

A) (1-{tert-Butyl-[1-(2-hydroxy-ethylcarbamoyl)-ethoxy]-amino}-2,2-dimethyl-propyl)-phosphonic acid diethyl ester In analogy to Example 3B) are reacted 9.7 g (0.056 mol) PMDTA, 5.54 g (0.056 mol) CuCl, 4.7 g (0.031 mol) 2-chloro-N-(2-hydroxy-ethyl)-propionamide and 8.3 g (0.028 mol) [1-tert-butyl-amino-N-oxyl]-2,2-dimethyl-propyl]-phosphonic acid diethyl ester (prepared as described by P. Tordo et al.: Macromolecules 33. 1141 (2000)) to afford 9.9 g of the title compound as a colorless oil.

$^1$H-NMR (300 MHz, CDCl$_3$, δ ppm): 8.56 (bs, 1H), 4.70-3.20 (m, 11H), 2.10-1.0 (m, 27H).

C) Compound 7, Tab. 1

In analogy to Example 3C) are reacted 8.43 g (0.0205 mol) (1-{tert-butyl-[1-(2-hydroxy-ethylcarbamoyl)-ethoxy]-amino}-2,2-dimethyl-propyl)-phosphonic acid diethyl ester, 2.08 g (0.025 mol) acryloylchloride and 3.2 ml (0.025 mol) triethylamine to afford the title compound as two diastereomers: 4.79 g of a colorless oil and 3.5 g of a white solid, mp 95-98° C.

The MS (APCI) of each isomer: M$^+$=464, for C$_{21}$H$_{41}$N$_2$O$_7$ calculated M=464.54.

Example 8

Acrylic acid 2-[2-(4-acryloyloxy-2,6-diethyl-2,3,6-trimethyl-piperidin-1-yloxy)-propionylamino]-ethyl ester (Compound 8, Tab. 1)

A) 2-(2,6-Diethyl-4-hydroxy-2,3,6-trimethyl-piperidin-1-yloxy)-N-(2-hydroxy-ethyl)-propionamide In analogy to Example 3B) are reacted 11.1 g (0.064 mol) PMDTA, 6.33 g (0.064 mol) CuCl, 5.33 g (0.07 mol) 2-chloro-N-(2-hydroxy-ethyl)-propionamide and 7.72 g (0.032 mol) 2,6-diethyl-2,3,6-trimethyl-piperidine-1-oxyl (prepared as described in U.S. Pat. No. 6,353,107 B1, example 2) to afford 11.57 g of the title compound as a colorless oil.

B) Compound 8, Tab. 1

In analogy to Example 3C) are reacted 8.25 g (0.025 mol) 2-(2,6-diethyl-4-hydroxy-2,3,6-trimethyl-piperidin-1-yloxy)-N-(2-hydroxy-ethyl)-propionamide, 7.8 ml (0.056 mol) triethylamine and 5.0 g (0.055 mol) acryloylchloride to afford 7.5 g of the title compound as a colorless resin.

MS (APCI): calculated C$_{23}$H$_{38}$N$_2$O$_6$ (438.57). found M$^+$=438.

Example 9

Terephthalic acid bis-{1-[1-(2-acryloyloxy-ethylcarbamoyl)-ethoxy]-2,6-diethyl-2,3,6-trimethyl-piperidin-4-yl}ester (Compound 9, Tab. 1)

a. A) Terephthalic acid bis-(2,6-diethyl-1-oxyl-2,3,6-trimethyl-piperidin-4-yl) ester To a solution of 25.72 g (0.12 mol) 2,6-diethyl-2,3,6-trimethyl-piperidine-1-oxyl in 30 ml pyridine and 80 ml dichloromethane are added 12.2 g (0.06 mol) terephthaloylchloride and 0.3 g 4-dimetylaminopyridine. The mixture after 72 h stirring at room temperature is diluted with 100 ml dichloromethane and washed with water (3×50 ml). The organic phase is dried over MgSO$_4$, evaporated and chromatographed on silica gel with hexane-ethylacetate (4:1) to afford 31.85 g of the title compound as a red resin.

B) Terephthalic acid bis-{2,6-diethyl-1-[1-(2-hydroxy-ethylcarbamoyl)-ethoxy]-2,3,6-trimethyl-piperidin-4-yl}ester In analogy to Example 3B) are reacted 10.4 g (0.06 mol) PMDTA, 5.94 g (0.06 mol) CuCl, 5.0 g (0.033 mol) 2-chloro-N-(2-hydroxy-ethyl)-propionamide and 8.38 g (0.015 mol) terephthalic acid bis-(2,6-diethyl-1-oxyl-2,3,6-trimethyl-piperidin-4-yl) ester to afford 6.25 g of the title compound as a colorless resin.

$^1$H-NMR (300 MHz, CDCl$_3$, δ ppm): 8.1 (bs, 4ArH), 6.8-6.6 (m, 2H), 5.6-3.3 (m, 14H), 2.6-0.7 (m, 50H).

C) Compound 9, Tab. 1

In analogy to Example 3C) are reacted 6.0 g (0.0076 mol) terephthalic acid bis-{2,6-diethyl-1-[1-(2-hydroxy-ethylcarbamoyl)-ethoxy]-2,3,6-trimethyl-piperidin-4-yl}ester, 2.65 ml (0.0091 mol) triethylamin and 1.65 g (0.0091 mol) acryloylchloride to afford 4.5 g of the title compound as a colorless resin.

$^1$H-NMR (300 MHz, CDCl$_3$, δ ppm): 8.1 (bs, 4ArH), 6.8-3.3 (m, 20H), 2.4-0.7 (m, 50H).

Example 10

2-Methyl-acrylic acid 2-[2-(2,6-diethyl-2,3,6-trimethyl-4-oxo-piperidin-1-yloxy)-propionyloxy]-ethyl ester (Compound 10. Tab. 1)

In analogy to Example 1B) are reacted: 10.61 g (0.05 mol) 2,6-diethyl-1-oxy-2,3,6-trimethyl-piperidin-4-one, 13.25 g (0.05 mol) 2-methyl-acrylic acid 2-(2-bromo-propionyloxy)-ethyl ester, 9.89 g (0.1 mol) CuCl and 17.33 g (0.1 mol) PMDTA to afford 16.0 g of the title compound as a yellow oil.

MS (APCI): calculated C$_{21}$H$_{35}$NO$_6$ (397.52). found M$^+$=397.

Example 11

2-Methyl-acrylic acid 1-[1-(2-acryloyloxy-ethoxy-carbonyl)-ethoxy]-2,6-diethyl-2,3,6-trimethyl-piperidin-4-yl ester (Compound 11, Tab. 1)

In analogy to Example 4) are reacted 2.5 g (6.5 mmol) of compound 1 (from Example 1B), 0.73 g (7.2 mmol) triethylamine and 0.75 g (7.2 mmol) methacryloylchloride to afford 1.4 g of the title compound as a colorless oil.

MS (APCI): calculated C$_{24}$H$_{39}$NO$_7$ (453.58). found M$^+$=453.

Example 12

Acrylic acid 2-[2-(4-acryloyloxy-2,6-diethyl-2,3,6-trimethyl-piperidin-1-yloxy)-propionyloxy]-ethyl ester (Compound 12, Tab. 1)

In analogy to Example 4) are reacted 2.5 g (6.5 mmol) of compound 1 (from Example 1B), 0.73 g (7.2 mmol) triethylamine and 0.65 g (7.2 mmol) acryloylchloride to afford 1.6 g of the title compound as a colorless oil.

MS (APCI): calculated $C_{23}H_{37}NO_7$ (439.55). found $M^+=439$.

Example 13

Acrylic acid 2-{(2-acryloyloxy-ethyl)-[2-(2,6-diethyl-2,3,6-trimethyl-4-oxo-piperidin-1-yloxy)-propionyl]-amino}-ethyl ester (Compound 13, Tab. 1)

A) 2-Chloro-N,N-bis-(2-hydroxy-ethyl)-propionamide

Diethanolamine (10.51 g, 0.1 mol) is added to 12.25 (0.1 mol) of 2-chloropropionic acid methylester. The mixture is stirred for 24 h at room temperature. The formed methanol is evaporated to afford 18.8 g of the title compound as slightly yellow oil.

$^1$H-NMR (300 MHz, CDCl$_3$, δ ppm): 4.84 (q, 1H), 4.0-3.3 (m, 10H), 1.68 (d, 3H).

B) Acrylic acid 2-[(2-acryloyloxy-ethyl)-(2-chloro-propionyl)-amino]-ethyl ester In analogy to Example 4) are reacted 17.0 g (0.087 mol) of 2-chloro-N,N-bis-(2-hydroxy-ethyl)-propionamide, 19.4 g (0.19 mol) triethylamine and 17.32 g (0.19 mol) acryloylchloride to afford 8.2 g of the title compound as a yellow oil.

TABLE 1

| Nr | Structure |
|---|---|
| 1 | (structure) |
| 2 | (structure) |
| 3 | (structure) |
| 4 | (structure) |
| 5 | (structure) |
| 6 | (structure) |

TABLE 1-continued
| Nr | Structure |
|---|---|
| 7 | 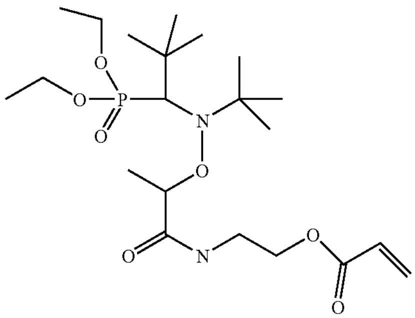 |
| 8 | 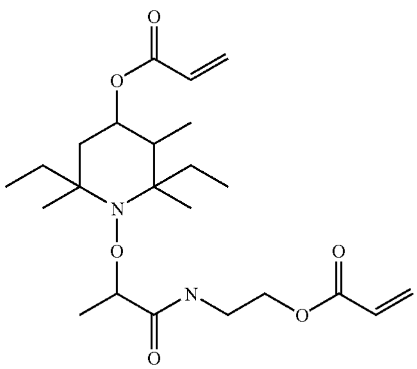 |
| 9 | 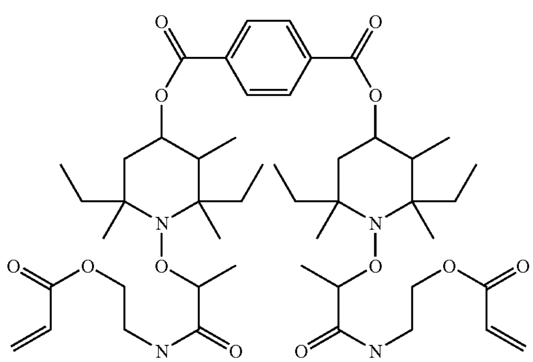 |
| 10 | 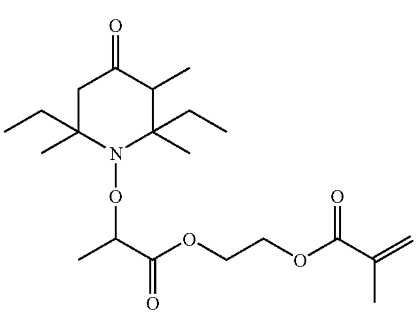 |
TABLE 1-continued
| Nr | Structure |
|---|---|
| 11 | |
| 12 | |
| 13 | |
The invention claimed is:
1. A compound of formula (I), (II) or (III)
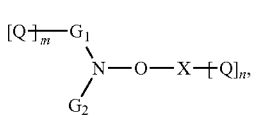
(I)
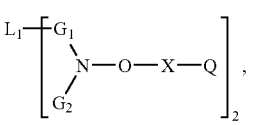
(II)
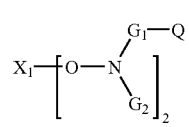
(III)

wherein Q is

[chemical structures shown]

wherein
R is independently H or $C_1$-$C_4$alkyl;
D is O or $NR_3$;
in formula (I) m and n independently are a number 0 or 1 wherein at least one of both is 1;
if in formula (I) m=0 and n=1

X is [chemical structures shown]

wherein
* denotes where the group is attached to the oxygen atom;
A is O or $NR_3$;
$B_1$ is $C_1$-$C_{25}$alkylene, which may be interrupted by O or $NR_3$ groups, $C_5$-$C_7$cycloalkylene which can contain O and or $NR_3$ groups in the ring, which both are unsubstituted or substituted by $C_1$-$C_8$alkoxy, halogen or a group —COO($C_1$-$C_{18}$alkyl) or phenylene;
additionally —A—$B_1$— can be a direct bond; or
if A is —O— and D is $NR_3$, $B_1$ can be a direct bond; or
if A is $NR_3$ and D is O or $NR_3$, $B_1$ can be a direct bond;
E is a direct bond or a —C(O)— group;
$R_1$, $R_2$ and $R_3$ are independently H, $C_1$-$C_{18}$alkyl, which is unsubstituted or substituted by $C_1$-$C_8$alkoxy, halogen or a group —COO($C_1$-$C_{18}$alkyl), $C_5$-$C_7$cycloalkyl, which is unsubstituted or substituted by $C_1$-$C_8$alkoxy, halogen or a group —COO($C_1$-$C_{18}$alkyl), phenyl, which is unsubstituted or substituted by $C_1$-$C_8$alkoxy, $C_1$-$C_8$alkyl, halogen or a group —COO($C_1$-$C_{18}$alkyl);
the group

[chemical structure with $G_1$, $G_2$, N]

is

[chemical structures shown]

A is as defined above; and
if A is O, $E_1$ is —$CH_2$—
if A is $NR_3$, $E_1$ is —C(O)—, —$CH_2$— or a direct bond;
$R_4$, $R_5$, $R_6$ are independently $C_1$-$C_{18}$alkyl, $C_5$-$C_7$cycloalkyl, $C_7$-$C_9$phenylalkyl or phenyl;
$R_7$, $R_8$ are independently H, $C_1$-$C_{18}$alkyl, $C_5$-$C_7$cycloalkyl, $C_7$-$C_9$phenylalkyl or $C_1$-$C_{18}$acyl;
L is a direct bond, O or $NR_7$;
$R_9$, $R_{10}$ are independently H or $C_1$-$C_{18}$alkoxy,
if $R_9$ is H, $R_{10}$ is additionally OH, —O—($C_1$-$C_{18}$)acyl, —$NR_3$—($C_1$-$C_{18}$)acyl or $N(R_3)_2$;
or
$R_9$ and $R_{10}$ together with the C-atom to which they are bonded form a cyclic ketale group

[chemical structures shown]

wherein k is 0, 1 or 2 and $R_{15}$ is $C_1$-$C_{18}$alkyl, —$CH_2$—OH or —$CH_2$—O—($C_1$-$C_{18}$)acyl; or
$R_9$ and $R_{10}$ together form the group =O, or =N—A—$R_7$;
$R_{11}$, $R_{12}$, $R_{13}$ and $R_{14}$ are independently of each other $C_1$-$C_4$alkyl;
if in formula (I) m=1 and n=1
X is as defined above;
the group

[chemical structure with $G_1$, $G_2$, N]

is

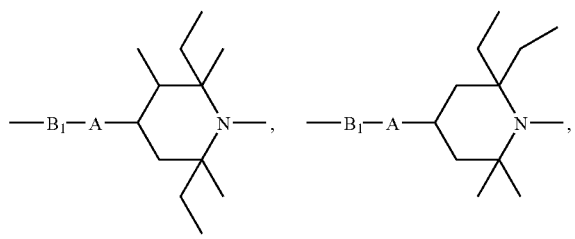

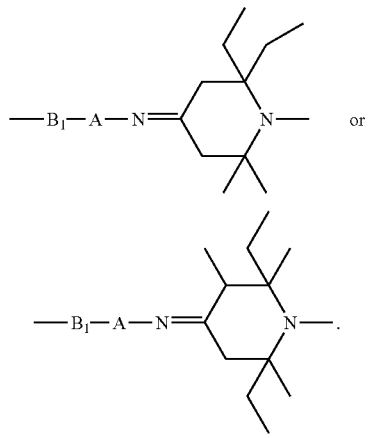

wherein
A and $B_1$ are as defined above;
if in formula (I) m=1 and n=0

X is

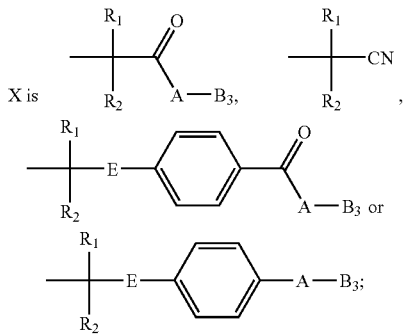

wherein A is O, $NR_3$ or a direct bond and E, $R_1$ and $R_2$ are as defined above;

$B_3$ is H, $C_1$-$C_{25}$alkyl, which may be interrupted by O or $NR_3$ groups, $C_5$-$C_7$cycloalkyl, which can contain O and or $NR_3$ groups in the ring, which both are unsubstituted or substituted by $C_1$-$C_8$alkoxy, halogen or a group —COO($C_1$-$C_{18}$alkyl) or $C_1$-$C_{18}$alkoxy or phenyl;

the group

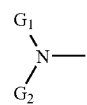

is

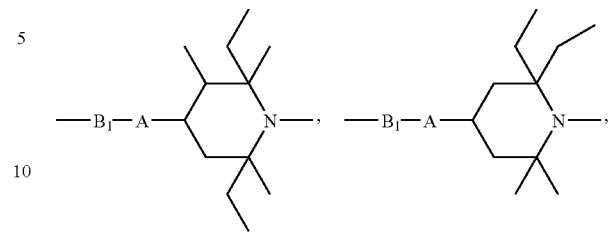

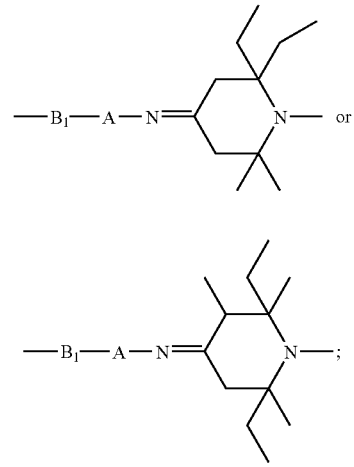

wherein
A and $B_1$ are as defined above;
in formula (II)

X is

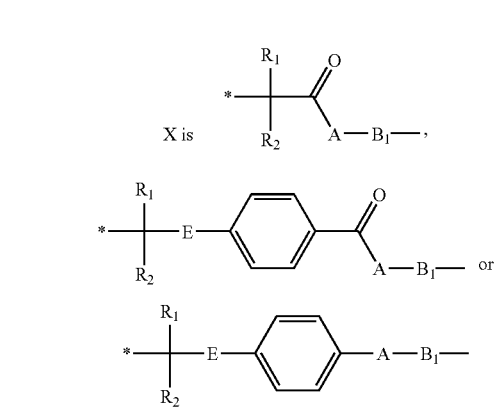

wherein
* denotes where X is attached to the oxygen atom and A, $B_1$, E, $R_1$ and $R_2$ are as defined above;

the group $$\begin{array}{c} G_1 \\ \diagdown \\ N- \\ \diagup \\ G_2 \end{array}$$

is

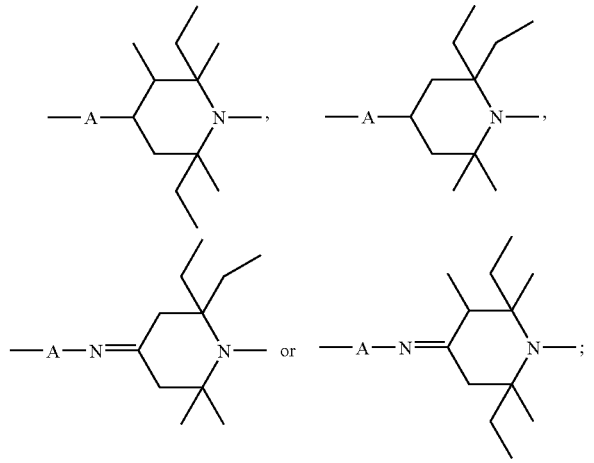

wherein A is as defined above;

L₁ is a divalent group derived from an aliphatic dicarboxylic acid having 2 to 18 carbon atoms from an aromatic dicarboxylic acid or from an aliphatic-aromatic dicarboxylic acid;

in formula (III)

X₁ is a group

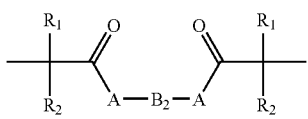

wherein $B_2$ is a direct bond, $C_1$-$C_{25}$alkylene, which may be interrupted by O or $NR_3$ groups, $C_5$-$C_7$cycloalkylene which can contain O and or $NR_3$ groups in the ring, which both are unsubstituted or substituted by $C_1$-$C_8$alkoxy, halogen or a group —COO($C_1$-$C_{18}$alkyl) or phenylene, wherein when $B_2$ is a direct bond one A is O and the other is $NR_3$;

A, $B_1$, $R_1$ and $R_2$ are as defined above and
the group

is

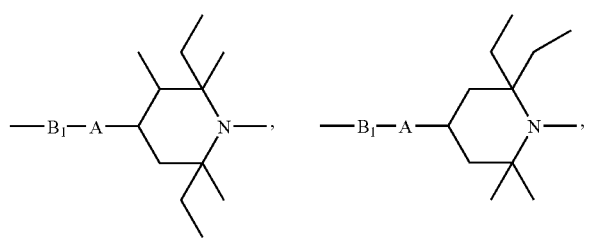

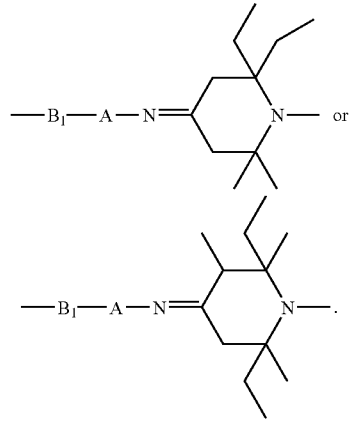

2. A compound according to claim 1 of formula (I), (II) or (III)

wherein Q is

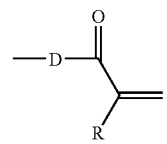

R is independently H or $C_1$-$C_4$alkyl; and

D is O or $NR_3$.

3. A compound according to claim 1 of formula (I), (II) or (III)

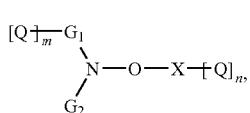

(I)

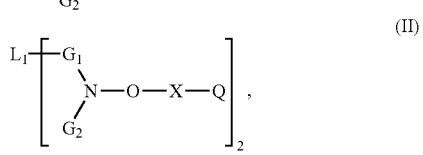

(II)

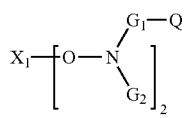

(III)

wherein Q is

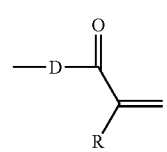

wherein
R is independently H or $C_1$-$C_4$alkyl;
D is O or $NR_3$;

in formula (I) m and n independently are a number 0 or 1 wherein at least one of both is 1;
if in formula (I) m=0 and n=1

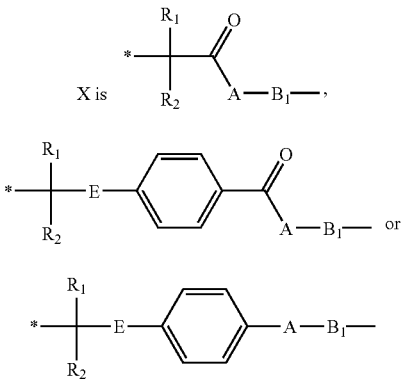

wherein
* denotes where the group is attached to the oxygen atom;
A is O or $NR_3$;
$B_1$ is $C_1$-$C_{25}$alkylene, which may be interrupted by O or $NR_3$ groups, $C_5$-$C_7$cycloalkylene which can contain O and or $NR_3$ groups in the ring, which both are unsubstituted or substituted by $C_1$-$C_8$alkoxy, halogen or a group —COO($C_1$-$C_{18}$alkyl) or phenylene;
additionally —A—$B_1$— can be a direct bond; or
if A is —O— and D is $NR_3$, $B_1$ can be a direct bond;
if A is $NR_3$ and D is O or $NR_3$, $B_1$ can be a direct bond;
E is a direct bond or a —C(O)— group;
$R_1$, $R_2$ and $R_3$ are independently H, $C_1$-$C_{18}$alkyl, which is unsubstituted or substituted by $C_1$-$C_8$alkoxy, halogen or a group —COO($C_1$-$C_{18}$alkyl), $C_5$-$C_7$cycloalkyl, which is unsubstituted or substituted by $C_1$-$C_8$alkoxy, halogen or a group —COO($C_1$-$C_{18}$alkyl), phenyl, which is unsubstituted or substituted by $C_1$-$C_8$alkoxy, $C_1$-$C_8$alkyl, halogen or a group —COO($C_1$-$C_{18}$alkyl);
the group

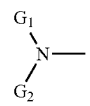

is

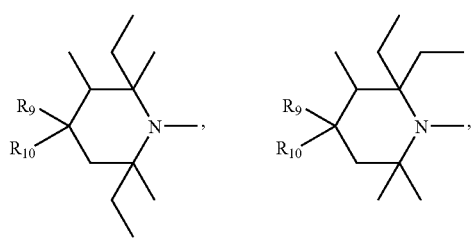

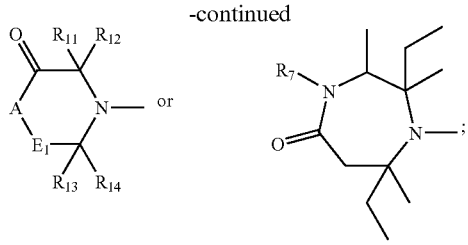

wherein
A is as defined above; and
if A is O, $E_1$ is —$CH_2$—
if A is $NR_3$, $E_1$ is —C(O)—, —$CH_2$— or a direct bond;
$R_7$ is H, $C_1$-$C_{18}$alkyl, $C_5$-$C_7$cycloalkyl, $C_7$-$C_9$phenylalkyl or $C_1$-$C_{18}$acyl;
$R_9$, $R_{10}$ are independently H or $C_1$-$C_{18}$alkoxy,
if $R_9$ is H, $R_{10}$ is additionally OH, —O—($C_1$-$C_{18}$)acyl, —$NR_3$—($C_1$-$C_{18}$)acyl or $N(R_3)_2$;
or
$R_9$ and $R_{10}$ together with the C-atom to which they are bonded form a cyclic ketale group

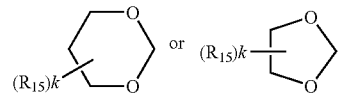

wherein k is 0, 1 or 2 and $R_{15}$ is $C_1$-$C_{18}$alkyl, —$CH_2$—OH or —$CH_2$—O—($C_1$-$C_{18}$)acyl; or
$R_9$ and $R_{10}$ together form the group =O, or =N—A—$R_7$;
if in formula (I) m=1 and n=1
X is as defined above;
the group

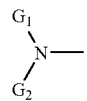

is

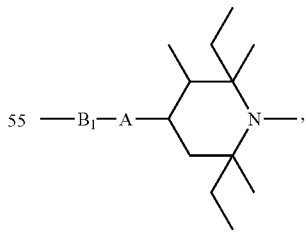

-continued

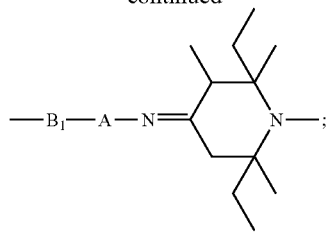

wherein
A and B₁ are as defined above;
if in formula (I) m=1 and n=0

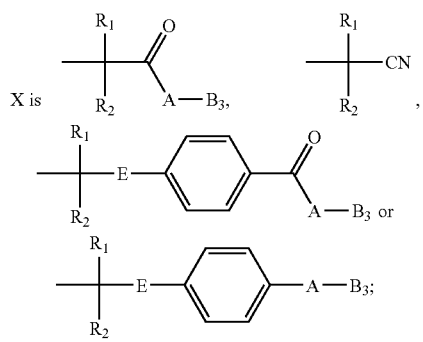

wherein A is O, NR₃ or a direct bond and E, R₁ and R₂ are as defined above;
B₃ is H, $C_1$-$C_{25}$alkyl, which may be interrupted by O or NR₃ groups, $C_5$-$C_7$cycloalkyl, which can contain O and or NR₃ groups in the ring, which both are unsubstituted or substituted by $C_1$-$C_8$alkoxy, halogen or a group —COO($C_1$-$C_{18}$alkyl) or $C_1$-$C_{18}$alkoxy or phenyl;
the group

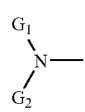

is

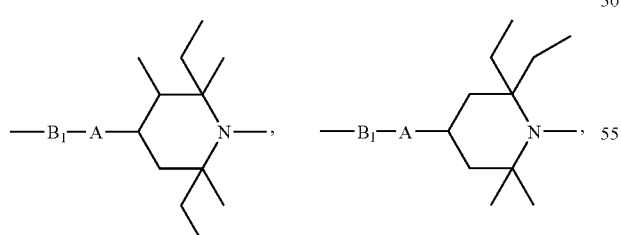

-continued

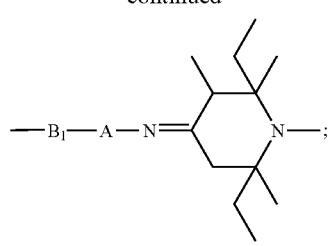

wherein
A and B₁ are as defined above;
in formula (II)

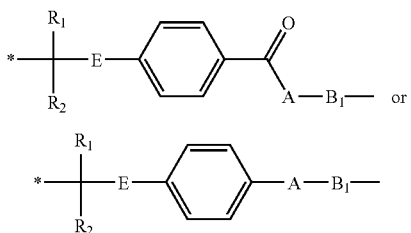

wherein
* denotes where X is attached to the oxygen atom and A, B₁, E, R₁ and R₂ are as defined above;
the group

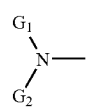

is

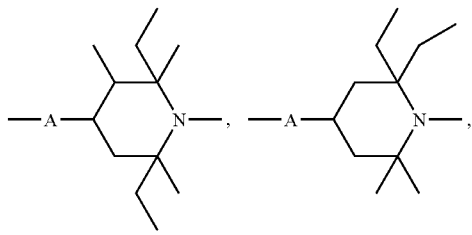

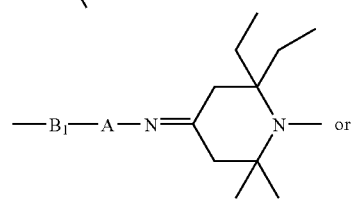

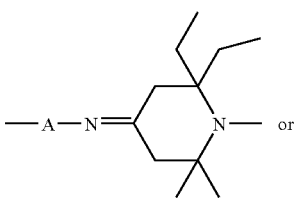

-continued

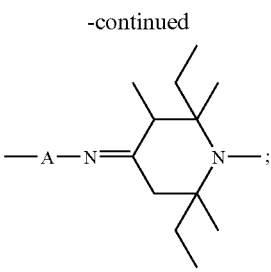

wherein A is as defined above;

L₁ is a divalent group derived from an aliphatic dicarboxylic acid having 2 to 18 carbon atoms from an aromatic dicarboxylic acid or from an aliphatic-aromatic dicarboxylic acid;

in formula (III)

X₁ is a group

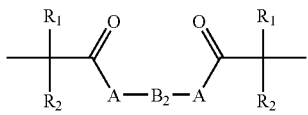

wherein B₂ is a direct bond, $C_1$-$C_{25}$alkylene, which may be interrupted by O or NR₃ groups, $C_5$-$C_7$cycloalkylene which can contain O and or NR₃ groups in the ring, which both are unsubstituted or substituted by $C_1$-$C_8$alkoxy, halogen or a group —COO($C_1$-$C_{18}$alkyl) or phenylene, wherein when B₂ is a direct bond one A is O and the other is NR₃;

A, B₁, R₁ and R₂ are as defined above and the group

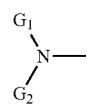

is

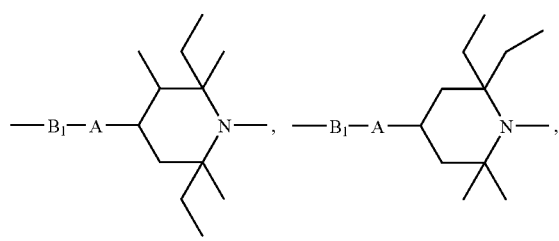

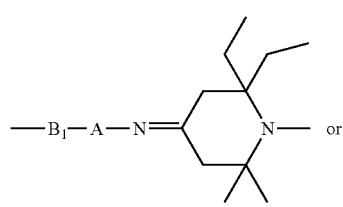

-continued

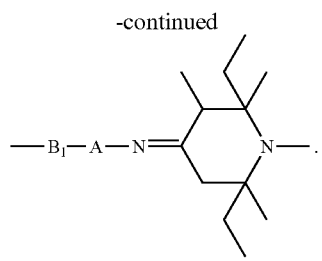

4. A compound according to claim 1 of formula (Ia)

$$\underset{G_2}{\overset{G_1}{N}}-O-X-Q \quad (Ia)$$

wherein

Q is

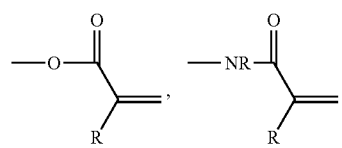

wherein R is independently H or $C_1$-$C_4$alkyl;

X is

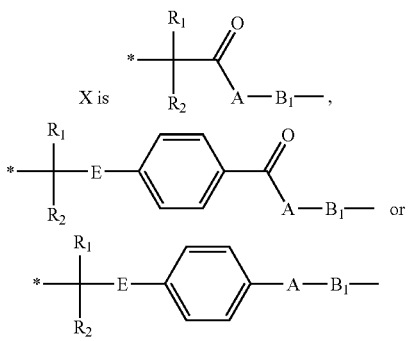

wherein

* denotes where X is attached to the oxygen atom;

A is O or NR₃;

B₁ is $C_1$-$C_{25}$alkylene, which may be interrupted by O or NR₃ groups, $C_5$-$C_7$cycloalkylene which can contain O and or NR₃ groups in the ring, which both are unsubstituted or substituted by $C_1$-$C_8$alkoxy, halogen or a group —COO($C_1$-$C_{18}$alkyl) or phenylene;

additionally —A—B₁— can be a direct bond; or if A is —O— and D is NR₃, B₁ can be a direct bond; or if A is NR₃ and D is O or NR₃, B₁ can be a direct bond;

E is a direct bond;

R₁, R₂ are H or CH₃;

R₃ is H, $C_1$-$C_{18}$alkyl, $C_5$-$C_6$cycloalkyl or phenyl;

the group

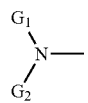

is

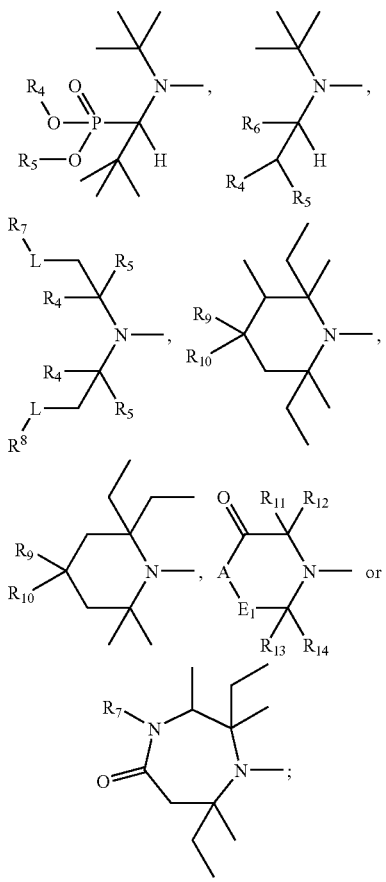

wherein
A is as defined above; and
if A is O, $E_1$ is —$CH_2$—
if A is $NR_3$, $E_1$ is —C(O)—, —$CH_2$— or a direct bond;
$R_4$, $R_5$, are methyl;
$R_7$, $R_8$ are independently H, $C_1$-$C_{18}$alkyl, $C_5$-$C_7$cycloalkyl, benzyl or $C_1$-$C_{18}$acyl;
L is a direct bond, O or $NR_7$;
$R_9$, $R_{10}$ are independently H or $C_1$-$C_{18}$alkoxy,
if $R_9$ is H, $R_{10}$ is additionally OH, —O—($C_1$-$C_{18}$)acyl, —$NR_3$—($C_1$-$C_{18}$)acyl or $N(R_3)_2$;
or
$R_9$ and $R_{10}$ together with the C-atom to which they are bonded form a cyclic ketale group

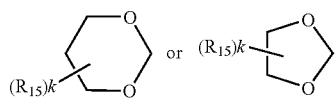

wherein k is 0, 1 or 2 and $R_{15}$ is $C_1$-$C_{18}$alkyl, —$CH_2$—OH or —$CH_2$—O—($C_1$-$C_{18}$)acyl; or
$R_9$ and $R_{10}$ together form the group =O, or =N—A—$R_7$;
$R_{11}$, $R_{12}$, $R_{13}$ and $R_{14}$ are independently of each other $C_1$-$C_4$alkyl.

5. A compound according to claim 4 of formula (Ia)

(Ia)

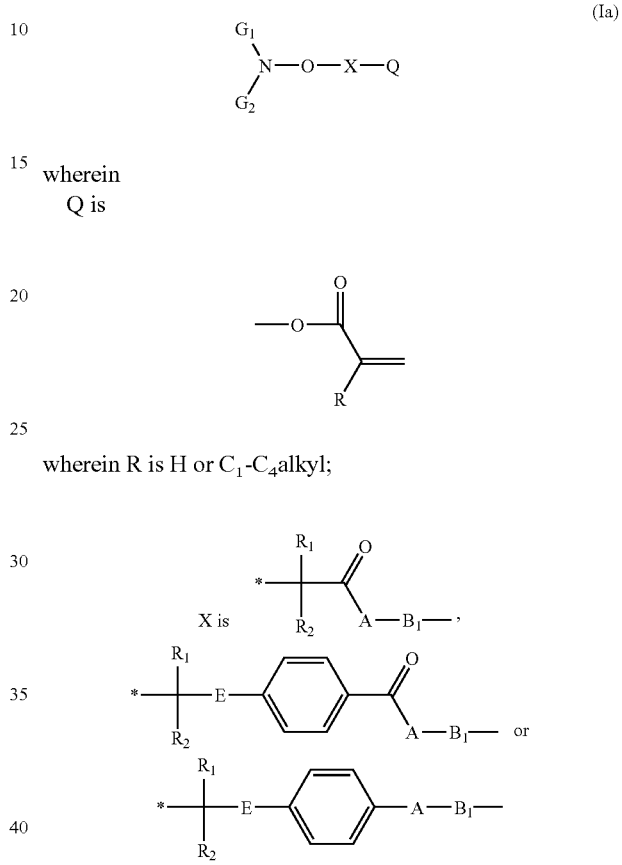

wherein
Q is wherein R is H or $C_1$-$C_4$alkyl;

X is wherein
* denotes where X is attached to the oxygen atom;
A is O or $NR_3$;
$B_1$ is $C_1$-$C_{25}$alkylene, which may be interrupted by O or $NR_3$ groups, $C_5$-$C_7$cycloalkylene which can contain O and or $NR_3$ groups in the ring, which both are unsubstituted or substituted by $C_1$-$C_8$alkoxy, halogen or a group —COO($C_1$-$C_{18}$alkyl) or phenylene;
additionally —A—$B_1$— can be a direct bond; or
if A is —O— and D is $NR_3$, $B_1$ can be a direct bond; or
if A is $NR_3$ and D is O or $NR_3$, $B_1$ can be a direct bond;
E is a direct bond;
$R_1$, $R_2$ are H or $CH_3$;
$R_3$ is H, $C_1$-$C_{18}$alkyl, $C_5$-$C_6$cycloalkyl or phenyl;
the group

is

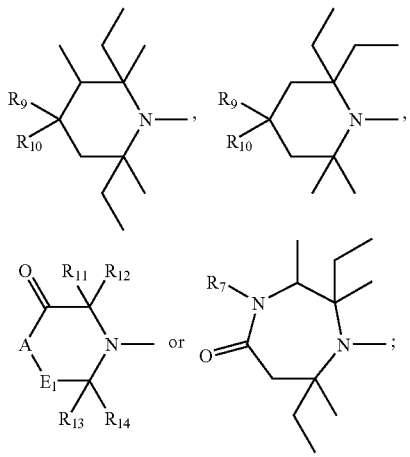

wherein
A is as defined above; and
if A is O, $E_1$ is —$CH_2$—
if A is $NR_3$, $E_1$ is —C(O)—, —$CH_2$— or a direct bond;
$R_7$ is H, $C_1$-$C_{18}$alkyl, $C_5$-$C_7$cycloalkyl, benzyl or $C_1$-$C_{18}$acyl;
$R_9$, $R_{10}$ are independently H or $C_1$-$C_{18}$alkoxy,
if $R_9$ is H, $R_{10}$ is additionally OH, —O—($C_1$-$C_{18}$)acyl, —$NR_3$—($C_1$-$C_{18}$)acyl or $N(R_3)_2$;
or
$R_9$ and $R_{10}$ together with the C-atom to which they are bonded form a cyclic ketale group

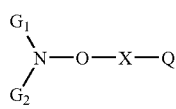

wherein k is 0, 1 or 2 and $R_{15}$ is $C_1$-$C_{18}$alkyl, —$CH_2$—OH or —$CH_2$—O—($C_1$-$C_{18}$)acyl; or
$R_9$ and $R_{10}$ together form the group =O, or =N—O—$R_7$;
$R_{11}$, $R_{12}$, $R_{13}$ and $R_{14}$ are independently of each other $C_1$-$C_4$alkyl.

6. A compound according to claim 5 of formula (Ia)

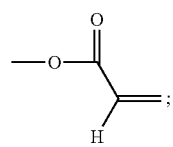

(Ia)

wherein
Q is

X is

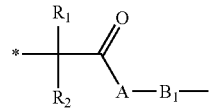

wherein
* denotes where X is attached to the oxygen atom;
A is O or $NR_3$;
$B_1$ is $C_1$-$C_{18}$alkylene, or phenylene;
$R_1$, $R_2$ are H or $CH_3$;
$R_3$ is H, $C_1$-$C_4$alkyl or phenyl;
the group

is

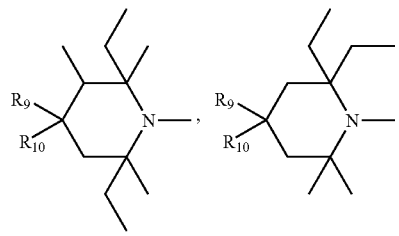

$R_9$, $R_{10}$ are independently H or $C_1$-$C_{18}$alkoxy, or
if $R_9$ is H, $R_{10}$ is additionally OH, —O—($C_1$-$C_{18}$)acyl, —$NR_3$—($C_1$-$C_{18}$)acyl or $N(R_3)_2$;
or
$R_9$ and $R_{10}$ together with the C-atom to which they are bonded form a cyclic ketale group

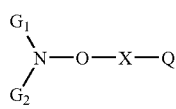

wherein k is 0, 1 or 2 and $R_{15}$ is $C_1$-$C_{18}$alkyl, —$CH_2$—OH or —$CH_2$—O—($C_1$-$C_{18}$)acyl; or
$R_9$ and $R_{10}$ together form the group =O, or =N—O—$R_7$;
$R_{11}$, $R_{12}$, $R_{13}$ and $R_{14}$ are independently of each other $C_1$-$C_4$alkyl.

7. A compound according to claim 6 of formula (Ia)

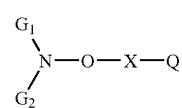

(Ia)

wherein
Q is

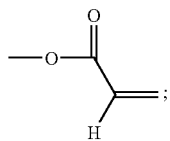

X is

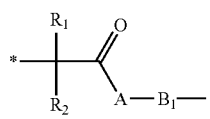

wherein
* denotes where X is attached to the oxygen atom;
A is O or NR$_3$;
B$_1$ is C$_1$-C$_4$alkylene, or phenylene;
R$_1$, R$_2$ are H or CH$_3$;
R$_3$ is H, C$_1$-C$_4$alkyl or phenyl;
the group

is

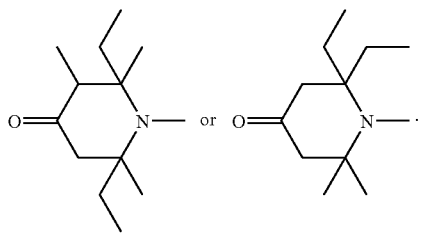

8. A compound according to claim 1, which is
a) Acrylic acid 2-[2-(2,6-diethyl-4-hydroxy-2,3,6-trimethyl-piperidin-1-yloxy)-propionyloxy]-ethyl ester
b) Acrylic acid 2-[2-(2,6-diethyl-2,3,6-trimethyl-4-oxo-piperidin-1-yloxy)-propionyloxy]-ethyl ester
c) Acrylic acid 2-[2-(2,6-diethyl-2,3,6-trimethyl-4-oxo-piperidin-1-yloxy)-2-methyl-propionylamino]ethyl ester
d) Acrylic acid 1-(1-{6-[2-(4-acryloyloxy-2,6-diethyl-2,3,6-trimethyl-piperidin-1-yloxy)-propionylamino]-hexylcarbamoyl}-ethoxy)-2,6-diethyl-2,3,6-trimethyl-piperidin-4-yl ester
e) 2-Methyl-acrylic acid 2-[2-(2,6-diethyl-2,3,6-trimethyl-4-oxo-piperidin-1-yloxy)-propionylamino]-ethyl ester
f) Acrylic acid 2-[2-(4-tert-butyl-2,2-diethyl-6,6-dimethyl-3-oxo-piperazin-1-yloxy)-propionylamino]-ethyl ester
g) Acrylic acid 2-(2-{N-tert-butyl-N-[1-(diethoxy-phosphoryl)-2,2-dimethyl-propyl]-aminooxy}propionylamino)-ethyl ester
h) Acrylic acid 2-[2-(4-acryloyloxy-2,6-diethyl-2,3,6-trimethyl-piperidin-1-yloxy)-propionylamino]-ethyl ester
i) Terephthalic acid bis-{1-[1-(2-acryloyloxy-ethylcarbamoyl)-ethoxy]-2,6-diethyl-2,3,6-trimethyl-piperidin-4-yl}ester
j) 2-Methyl-acrylic acid 2-[2-(2,6-diethyl-2,3,6-trimethyl-4-oxo-piperidin-1-yloxy)-propionyloxy]-ethyl ester
k) 2-Methyl-acrylic acid 1-[1-(2-acryloyloxy-ethoxycarbonyl)-ethoxy]-2,6-diethyl-2,3,6-trimethyl-piperidin-4-yl ester
l) Acrylic acid 2-[2-(4-acryloyloxy-2,6-diethyl-2,3,6-trimethyl-piperidin-1-yloxy)-propionyloxy]-ethyl ester
m) Acrylic acid 2-{(2-acryloyloxy-ethyl)-[2-(2,6-diethyl-2,3,6-trimethyl-4-oxo-piperdin-1-yloxy)-propionyl]-amino}-ethyl ester.

9. A polymerizable composition comprising
a) at least one ethylenically unsaturated monomer;
b) a radical polymerization initiator; and
c) a compound of formula (I), (II) or (III) according to claim 1.

10. A polymerizable composition according to claim 9 wherein the ethylenically unsaturated monomer is selected from the group consisting of ethylene, propylene, n-butylene, i-butylene, styrene, substituted styrene, conjugated dienes, acrolein, vinyl acetate, vinylpyrrolidone, vinylimidazole, maleic anhydride, (alkyl)acrylic acidanhydrides, (alkyl) acrylic acid salts, (alkyl)acrylic esters, (alkyl)acrylonitriles, (alkyl)acrylamides, vinyl halides or vinylidene halides.

11. A polymerizable composition according to claim 10 wherein the ethylenically unsaturated monomer is a compound of formula $CH_2=C(R_a)-(C=Z)-R_b$, wherein Z is O or S;
R$_a$ is hydrogen or C$_1$-C$_4$alkyl;
R$_b$ is NH$_2$, O$^-$(Me$^+$), glycidyl, unsubstituted C$_1$-C$_{18}$alkoxy, C$_2$-C$_{100}$alkoxy interrupted by at least one N and/or O atom, or hydroxy-substituted C$_1$-C$_{18}$alkoxy, unsubstituted C$_1$-C$_{18}$alkylamino, di(C$_1$-C$_{18}$alkyl)amino, hydroxy-substituted C$_1$-C$_{18}$alkylamino or hydroxy-substituted di(C$_1$-C$_{18}$alkyl)amino, —O—CH$_2$—CH$_2$—N(CH$_3$)$_2$ or —O—CH$_2$—CH$_2$—N$^+$H(CH$_3$)$_2$ An$^-$;
An$^-$ is a anion of a monovalent organic or inorganic acid;
Me is a monovalent metal atom or the ammonium ion.

12. A polymerizable composition according to claim 9 wherein the radical polymerization initiator is a azo compound, a peroxide, a perester or a hydroperoxide.

13. A process for preparing an oligomer, a cooligomer, a polymer or a copolymer (block, random or graft) by free radical polymerization of at least one ethylenically unsaturated monomer or oligomer, which comprises (co)polymerizing the monomer or monomers/oligomers in the presence of
a) a free radical initiator; and
b) a compound of formula (I), (II) or (III) according to claim 1.

14. A process according to claim 13 wherein polymerization is carried out by applying heat or electromagnetic radiation from microwaves to γ-radiation.

15. A process according to claim 13 wherein the polymerization is carried out by heating and takes place at a temperature between 0° C. and 160° C.

16. A process according to claim 13 wherein the amount of component b) is from 1% to 100% by weight, based on the weight of the sum of all ethylenically unsaturated compounds.

17. A polymeric or oligomeric macroinitiator obtainable by a process according to claim 13.

18. A process for preparing a comb, star, tapered or branched polymer or copolymer by controlled free radical polymerization (CFRP), which comprises polymerizing at least one ethylenically unsaturated monomer in the presence of the polymeric macroinitiator obtainable in a process according to claim 13.

19. A process according to claim 18 wherein the polymerization is carried out by heating and takes place at a temperature between 80° C. and 160° C.

* * * * *